United States Patent
Kompella et al.

(10) Patent No.: US 9,562,015 B2
(45) Date of Patent: Feb. 7, 2017

(54) METHODS AND COMPOSITIONS FOR ENHANCED DRUG DELIVERY TO THE EYE AND EXTENDED DELIVERY FORMULATIONS

(71) Applicant: The Regents of the University of Colorado, Denver, CO (US)

(72) Inventors: Uday B. Kompella, Englewood, CO (US); Ashish Thakur, Cincinnati, OH (US)

(73) Assignee: THE REGENTS OF THE UNIVERSITY OF COLORADO, A BODY, Denver, CO (US)

(*) Notice: Subject to any disclaimer, the term of this patent is extended or adjusted under 35 U.S.C. 154(b) by 0 days.

(21) Appl. No.: 14/359,146

(22) PCT Filed: Nov. 16, 2012

(86) PCT No.: PCT/US2012/065620
§ 371 (c)(1),
(2) Date: May 19, 2014

(87) PCT Pub. No.: WO2013/074988
PCT Pub. Date: May 23, 2013

(65) Prior Publication Data
US 2014/0309200 A1 Oct. 16, 2014

Related U.S. Application Data

(60) Provisional application No. 61/561,256, filed on Nov. 17, 2011.

(51) Int. Cl.
| | | |
|---|---|---|
| C07D 213/12 | (2006.01) |
| A61K 31/415 | (2006.01) |
| C07D 231/12 | (2006.01) |
| C07D 498/22 | (2006.01) |
| A61K 31/58 | (2006.01) |

(52) U.S. Cl.
CPC .......... *C07D 231/12* (2013.01); *A61K 31/415* (2013.01); *A61K 31/58* (2013.01); *C07D 498/22* (2013.01)

(58) Field of Classification Search
CPC ..... C07D 231/12; C07D 498/22; A61K 31/58; A61K 31/415
See application file for complete search history.

(56) References Cited

U.S. PATENT DOCUMENTS

| | | |
|---|---|---|
| 3,840,597 A | 10/1974 | Moore et al. |
| 4,221,787 A | 9/1980 | Bodor et al. |
| 4,469,689 A | 9/1984 | Anderson et al. |
| 5,145,684 A | 9/1992 | Liversidge et al. |
| 5,399,363 A | 3/1995 | Liversidge et al. |
| 5,494,683 A | 2/1996 | Liversidge et al. |
| 5,510,118 A | 4/1996 | Bosch et al. |
| 5,518,187 A | 5/1996 | Bruno et al. |
| 5,524,270 A | 6/1996 | Haess et al. |
| 5,718,388 A | 2/1998 | Czekai et al. |
| 5,862,999 A | 1/1999 | Czekai et al. |
| 6,267,989 B1 | 7/2001 | Liversidge et al. |
| 2003/0219490 A1 | 11/2003 | Hovey et al. |
| 2004/0033267 A1 | 2/2004 | Merisko-Liversidge et al. |
| 2005/0008707 A1 | 1/2005 | Hovey et al. |
| 2010/0056488 A1 | 3/2010 | Teicher et al. |
| 2011/0118303 A1* | 5/2011 | Vizioli .............. C07C 309/15 514/301 |

FOREIGN PATENT DOCUMENTS

| | | | |
|---|---|---|---|
| CN | 101805290 A | 8/2010 | |
| WO | 9738986 A1 | 10/1997 | |
| WO | 9746520 A1 | 12/1997 | |
| WO | 02083655 A1 | 10/2002 | |
| WO | WO 02083655 A1 * | 10/2002 | ........... A61K 9/0019 |
| WO | 2004037798 A1 | 5/2004 | |
| WO | 2004043934 A1 | 5/2004 | |
| WO | 2012016314 A1 | 2/2012 | |
| WO | 2012064130 A2 | 5/2012 | |
| WO | WO 2012064130 A2 * | 5/2012 | ........... A61K 31/415 |

OTHER PUBLICATIONS

Malik et al. "Hydrophilic prodrug approach for reduced pigment binding and enhanced transscleral retinal delivery of celecoxib" Mol. Pharm. 2012, 9, 605-614.*
Qandil et al. "Chemical and in vitro enzymatic stability of newly synthesized celecoxib lipophilic and hydrophilic amides" Int. J. Pharm. 2011, 416, 85-96.*
Ruiz et al. "A double prodrug system for colon targeting of benzenesulfonamide COX-2 inhibitors" Bioorg. Med. Chem. Lett. 2011,21.*
International Search Report and Written Opinion dated Mar. 15, 2013 for PCT International Application No. PCT/US2012/065620, pp. 1-25.
Jung et al., "Prednisolone 21-Sulfate Sodium: A Colon-Specific Prodrug of Prednisolone," 2003, vol. 55, pp. 1075-1082.
Extended European Search Report issued Apr. 8, 2015 in EP 12850433.9 (14 pages).
Shrivastava et al., "Dextran carrier macromolecule for colon specific delivery of celecoxib", Curr Drug Deliv. Apr. 7, 2010(2):144-51 [abstract].
Mamidi et al., "Pharmacological and Pharmacokinetic Evaluation of Celecoxib Prodrugs in Rats", Biopharmaceutics & Drug Disposition, 2002, 23:273-282.

(Continued)

*Primary Examiner* — Joseph Kosack
*Assistant Examiner* — Amanda L Aguirre
(74) *Attorney, Agent, or Firm* — Fisherbroyles, LLP; Jason M. Pass

(57) ABSTRACT

The present invention comprises compounds and compositions thereof for enhanced drug delivery. Pro-drug and double pro-drug derivatives of corticosteroids non-steroid anti-inflammatory drugs (NSAIDs), and ruboxistaurin for delivery to the eye are provided. The compounds and compositions are useful for treating various ocular diseases, including ocular diseases effecting the posterior segments of the eye. In addition, the present invention is directed to particle in particle carrier formulations for sustained release of therapeutic agents.

8 Claims, 26 Drawing Sheets

(56) References Cited

OTHER PUBLICATIONS

Ruiz et al., "A double prodrug system for colon targeting of benzenesulfonamide COX-2 inhibitors", Bioorganic & Medicinal Chemistry Letters 21 (2011) 6636-6640.
Qandil et al., "Chemical and in vitro enzymatic stability of newly synthesized celecoxib lipophilic and hydrophilic amides", International Journal of Pharmaceutics 416 (2011) 85— 96.
Pericherla et al., "Chemical Modifications of Nimesulide", J. Braz. Chem. Soc., vol. 18, No. 2, 384-390, 2007.
Malik et al., "Hydrophilic Prodrug Approach for Reduced Pigment Binding and Enhanced Transscleral Retinal Delivery of Celecoxib", Mol Pharm. Mar. 5, 2012;9(3):605-14.
Ayalasomayajula and Kompella, "Celecoxib, a selective cyclooxygenase-2 inhibitor, inhibits retinal vascular endothelial growth factor expression and vascular leakage in a streptozotocin-induced diabetic rat nwdel", Eur J Pharmacol, 2003. 458(3): p. 283-9.
Ayalasomayajula, et al., "Inhibition of cyclooxygenase-2, but not cyclooxygenase-1, reduces prostaglandin E2 secretion from diabetic rat retina", Eur J Pharmacol, 2004. 498(1-3): p. 275-8.
Ball and Dickson, "Displaced amacrine and ganglion cells in the newt retina", Exp Eye Res, 1983. 36(2): p. 199-213.
Cheng, et al., "Prostaglandin E2 induces vascular endothelial growth factor and basic fibroblast growth factor mRNA expression in cultured rat Afuller cells", Invest Ophthalmol Vis Sci, 1998. 39(3): p. 581-91.
Cheruvu and Kompella, 'Bovine and porcine transscleral solute transport: influence of lipophilicity and the Choroid-Bruch's layer, Invest Ophthalmol Vis Sci, 2006.47(10): p. 4513-22.
Derevjanik, et al., "Quantitative assessment of the integrity of the bloodretinal barrier in mice", Invest Ophthalmol Vis Sci, 2002. 43(7): p. 2462-7.
Ehinger, B., "Glial uptake of taurine in the rabbit retina", Brain Res, 1973. 60(2): p. 512-6.
Kadam, et al., "Sclera-choroid-RPE transport of eight beta-blockers in human, bovine, porcine, rabbit, and rat models", Invest Ophthalmol Vis Sci, 2011. PMID: 21282583.
Kompella, et al., "Subconjunctival nanoand microparticles sustain retinal delivery ofbudesonide, a corticosteroid tapable of inhibiting VEGF expression", Invest Ophthalmol Vis Sci, 2003. 44(3): p. 1192-201.
Obrosova, et al., "Antioxidants attenuate early up regulation of retinal vascular endothelial growth factor in streptozotocin-diabetic rats", Diabetologia, 2001. 44(9): p. 1102-10.
Penn, et al., "Vascular endothelial growth factor in eye disease", Prog Retin Eye Res, 2008.27(4): p. 331-71.
Pourcho, R.G., "Distribution of [35S]taurine in mouse retina after intravitreal and intravascular injection," Exp Eye Res, 1977. 25(2): p. 119-27.
Pow, et al., "Localization of taurine transporters, taurine, and (3)H taurine accumulation in the rat retina, pituitary, and brain", Glia, 2002. 37(2):p. 153-68.
Rohdewald and Keuth, "Evaluation ofalgesimetric parameters on the basis of tooth pulp stimulation in humans", Anesth Prog, 1990. 37(1): p. 4-10.
Saishin, et al., "Inhibition of protein kinase C decreases prostaglandin induced breakdown of the blood-retinal barrier," J Cell Physio1, 2003. 195(2):p. 210-9.
Sennlaub, et al., "Cycloo:Aygenase-2 in human and experimental ischemic proliferative retinopathy", Circulation, 2003. 108(2): p. 198-204.

\* cited by examiner

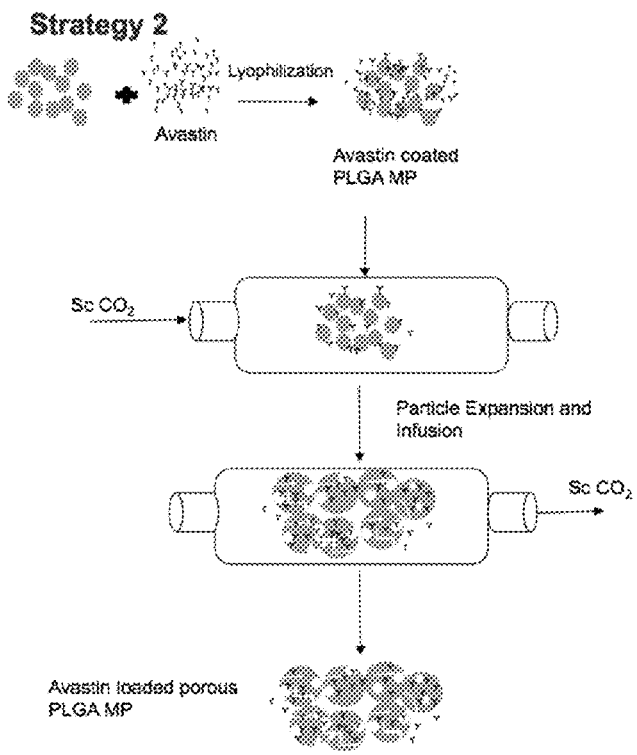
1) Plain PLGA microparticles are incubated with avastin and lyophilized
2) The avastin surface coated PLGA MP are treated with SCF
3) During the SCF treatment the PLGA MP expands with pore formation
4) Simultaneously, the avastin penetrates inside the MP due the pressure applied
5) The release was observed to be fast due to the removal of avastin from pores
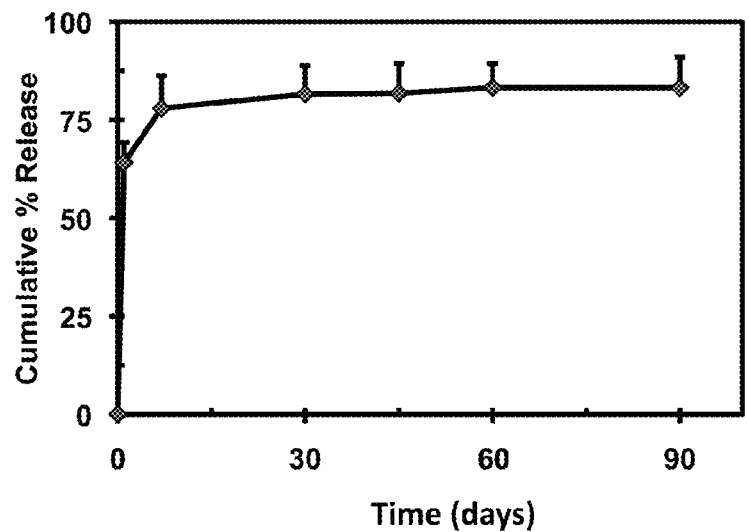
Figure 15

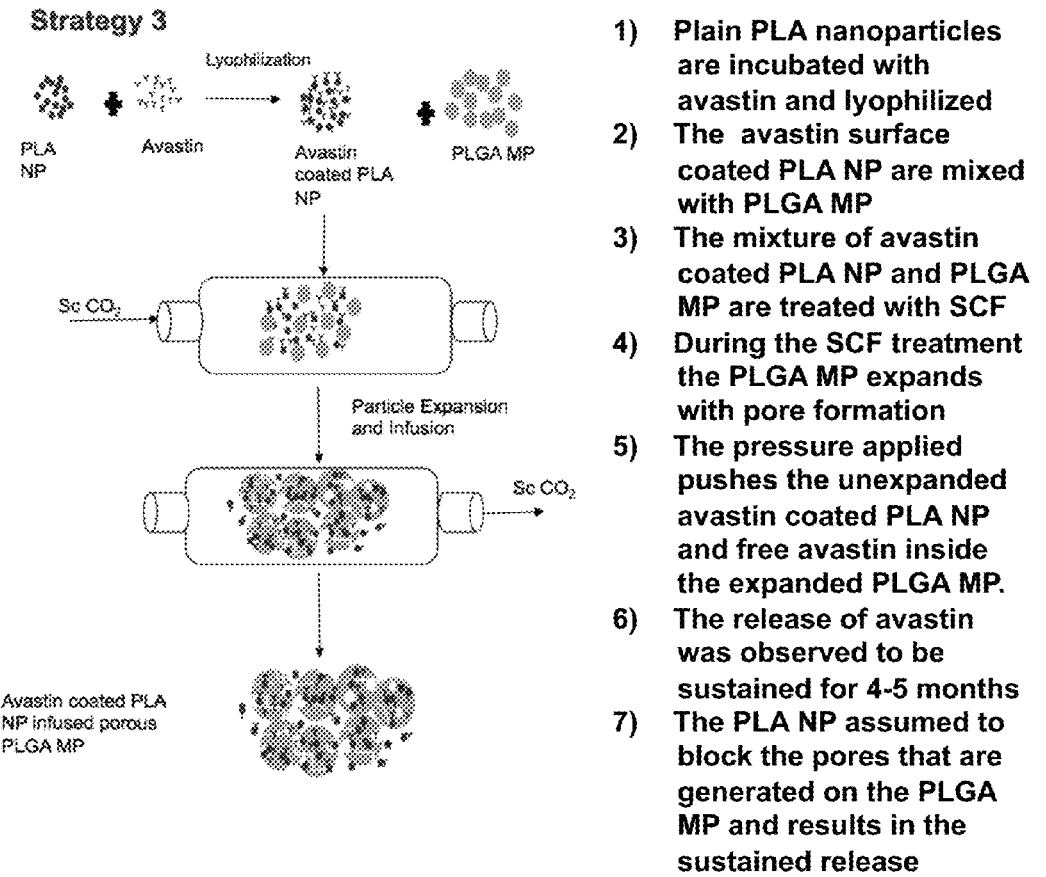

1) Plain PLA nanoparticles are incubated with avastin and lyophilized
2) The avastin surface coated PLA NP are mixed with PLGA MP
3) The mixture of avastin coated PLA NP and PLGA MP are treated with SCF
4) During the SCF treatment the PLGA MP expands with pore formation
5) The pressure applied pushes the unexpanded avastin coated PLA NP and free avastin inside the expanded PLGA MP.
6) The release of avastin was observed to be sustained for 4-5 months
7) The PLA NP assumed to block the pores that are generated on the PLGA MP and results in the sustained release

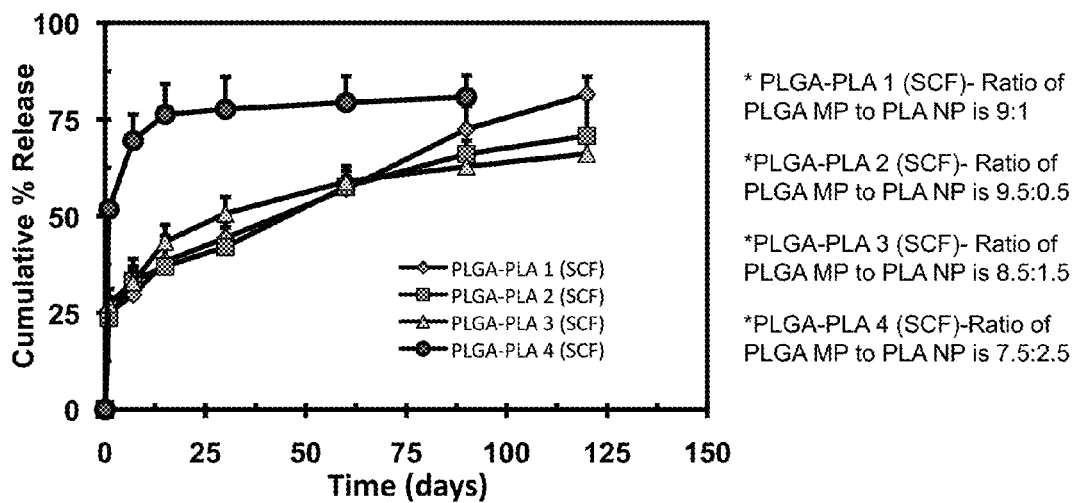

* PLGA-PLA 1 (SCF)- Ratio of PLGA MP to PLA NP is 9:1

*PLGA-PLA 2 (SCF)- Ratio of PLGA MP to PLA NP is 9.5:0.5

*PLGA-PLA 3 (SCF)- Ratio of PLGA MP to PLA NP is 8.5:1.5

*PLGA-PLA 4 (SCF)-Ratio of PLGA MP to PLA NP is 7.5:2.5

Figure 16

METHODS AND COMPOSITIONS FOR ENHANCED DRUG DELIVERY TO THE EYE AND EXTENDED DELIVERY FORMULATIONS

CROSS-REFERENCE TO RELATED APPLICATIONS

This application is a 35 U.S.C. §371 national stage application of International Patent Application No. PCT/US2012/65620 filed on Nov. 16, 2012, which claims priority to U.S. Provisional Patent Application No. 61/561,256 filed on Nov. 17, 2011. The contents of the above-identified priority documents are hereby fully incorporated herein by reference.

STATEMENT REGARDING FEDERALLY SPONSORED RESEARCH OR DEVELOPMENT

This invention was made with government support under grant number EY018940 awarded by the National Institutes of Health. The government has certain rights in the invention.

FIELD OF THE INVENTION

The present invention relates generally to compounds and compositions thereof for enhanced drug delivery, and more specifically to pro-drug derivatives of corticosteroids and non-steroid anti-inflammatory drugs (NSAIDs) and ruboxistaurin adapted for delivery to posterior segments of the eye. In addition, the present invention is directed to carrier formulations for sustained release of therapeutic agents.

SUMMARY OF THE INVENTION

The present invention is directed to compounds with improved retinal delivery and efficacy and their use in treating retinal ocular disease. In addition, the present invention is directed to extended release formulations formed under inert conditions that maintain stability of the therapeutic agent while providing the desired extended release effect.

In one aspect, the present invention is directed to pro-drugs of corticosteroids. In one exemplary embodiment, the corticosteroids are lipophilic corticosteroids that have been modified to include one or more terminal hydrophilic acid functional group. In one exemplary embodiment, the terminal hydrophilic acid functional group is attached to the R at carbon 21 of the steroid backbone. Exemplary hydrophilic functional groups include, but are not limited to sulfates, phosphates, succinates, or salts thereof. In one exemplary embodiment, the corticosteroid is budesonide. In another exemplary embodiment, the hydrophilic acid functional group is a sulfate functional group. An example of a suitable sulfate functional group salt is a sulfate triethylammonium salt. In yet another, exemplary embodiment, the hydrophilic acid functional group is a succinate.

In another aspect, the present invention is directed to single and double pro-drugs of NSAIDs. The NSAIDs of the present invention may be modified to mask basic or mildly basic terminal functional groups with one or more multi-functional acid groups. Exemplary multi-functional acid groups include, but are not limited to, maleates, fumarates, tartates, citrates, and succinates. In one exemplary embodiment, the multi-functional acid group is a succinate. In certain exemplary embodiment, the NSAID may be further modified to include a taurine. The taurine may be bound to the multi-functional acid group, or directly to the parent molecule. In one exemplary embodiment, the NSAID is a coxib. In another exemplary embodiment, the coxib is celecoxib.

In yet another aspect, the present invention is directed to single and double pro-drugs of ruboxistaurin. In one exemplary embodiment, the pro-drug is a ruboxistaurin succinamidic acid. In certain exemplary embodiments, the ruboxistaurin may be further modified to include taurine.

In another aspect, the present invention is directed to methods of treating retinal ocular disease using the above pro-drug compounds. Ocular diseases that may be treated with compositions of the present invention include ocular degenerative diseases, ocular vascular diseases, ocular infectious diseases, and inflammatory ocular diseases. In one exemplary embodiment, the ocular disease is diabetic retinopathy. In certain exemplary embodiment, the corticosteroid pro-drug is formulated for transcleral delivery. In another exemplary embodiment, the NSAID pro-drug is formulated for topical administration to the eye in the form of eye drops.

In another aspect, the present invention is directed to particle-in-particle (PinP) extended release compositions. The PinP compositions comprises an inner particle which is infused within an outer particle. In one exemplary embodiment the inner particles are made from a material that will not expand upon exposure to a super critical fluids (SCF), such as super critical carbon dioxide, and the outer particle is made from a material that will expand upon exposure to SCF. Therapeutic agents may be loaded on the surface of the inner particle or outer particle, contained within the inner particle or outer particle, or contained within the pores of the outer particle, or a combination thereof. In one exemplary embodiment, the therapeutic agent is a small molecule based therapeutic agent, a nucleic acid-based therapeutic agent, a viral vector, or a peptide-based agent. In another exemplary embodiment, the therapeutic agent is a peptide-based agent.

BRIEF DESCRIPTION OF THE DRAWINGS

FIG. 15 is a schematic showing an alternative process for loading PLGA microparticles with bevacizumab using SCF and the corresponding release rate of bevacizumab from those particles.

FIG. 16 is schematic showing the initial loading of bevacizumab on PLA nanoparticles following by nanoparticle infusion into and expansion of PLGA microparticles using SCF according to an exemplary embodiment of the present invention and the resulting extended release profiles of bevacizumab from those particles.

DETAILED DESCRIPTION

Figure 1:
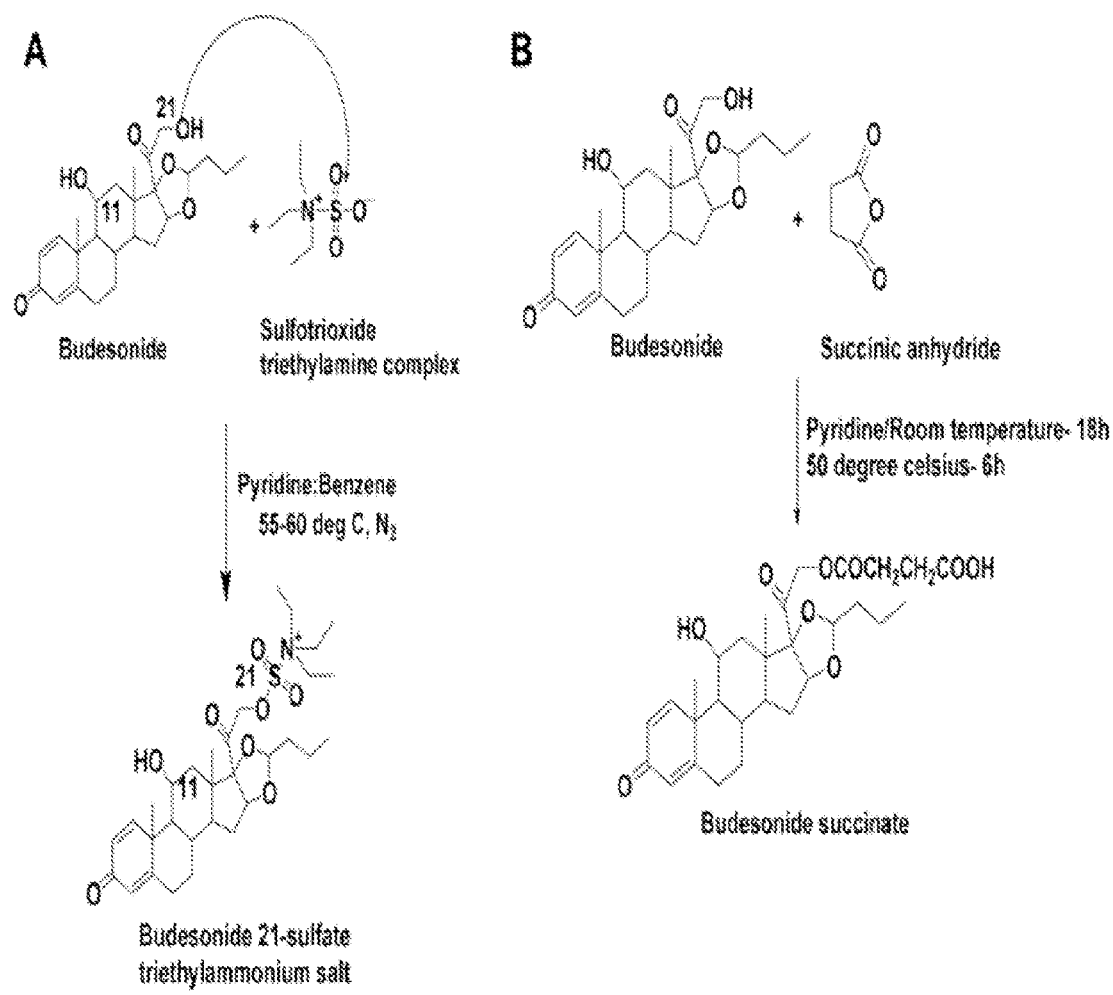
FIG. 1 is a schematic of a synthetic pathway for generating a) budesonide 21-sulfate triethylammonium salt and b) budesonide succinate according to an exemplary embodiment of the present invention.

As used herein "retina and retinal" refers both to the retina as well as the general posterior segment of the eye adjacent to the retina.

As used herein "treating or treatment" refers to a complete reversal or elimination of the underlying disease, a temporary or sustained prevention of disease progression, a temporary or sustained regression of the disease, and amelioration of one or more symptoms associated with the disease.

There are a number of ocular diseases that affect posterior segments of the eye, including the retina. Treatment of diseases affecting the posterior segment of the eye have typically included topical, systemic and intravitreal administration of therapeutic agents. Therapeutic agents administered topically must traverse the cornea, lens, trabecular network, and blood-aqueous barrier to reach the retina, with the net result that very little therapeutic agent generally reaches the posterior segment of the eye. Systemic administration requires traversal of the blood-retinal-barrier often requiring high doses that can lead to unwanted side effects. Intravitreal administration is highly invasive and carries the risks of retinal detachment, endophthalmitis and cataract. Accordingly, ideal therapeutic agents would not only exert the desired pharmacological effect, but traverse the unique ocular barriers of the eye and exert a localized effect at the site of disease.

A number of corticosteroids have shown promise in treating retinal diseases. However, corticosteroids have been limited by poor solubility and permeability profiles across the back of the eye. Accordingly, in one aspect, the present invention is directed to pro-drugs of corticosteroids with enhanced retinal delivery profiles and their use in treating retinal ocular diseases. In addition, a number of NSAIDs also possess pharmacological effects useful in treating ocular diseases, but as with corticosteroids, suffer from poor solubility, limited permeability of the eye, or a combination thereof. Accordingly, in another aspect, the present invention is directed to single and double pro-drugs of NSAIDs and their use in treating retinal ocular disease. The double prodrug concept can be applied to corticosteroids as well as other drugs. Further, it is often desirable to obtain sustained or extended delivery when delivering therapeutic agents, including those described above. When formulating therapeutic agents for extended delivery it is often necessary to rely upon a carrier that can control the rate of release of the therapeutic agent. Direct loading of a therapeutic agent on a carrier may fail to exert the desired or optimal extended release effect. Likewise encapsulation of certain therapeutic agents in a carrier can adversely affect the therapeutic agents stability as a result of the reaction conditions necessary to encapsulate the therapeutic agent in the carrier. Accordingly, in another aspect, the present invention is directed to extended release formulations that allow therapeutic agents to be loaded within extended release carriers under inert conditions.

Corticosteroid Pro-Drugs

Corticosteroids are a group of natural and synthetic analogues of the hormones secreted by the hypothalamic-anterior pituitary-adrenocortical (HPA) axis. These include glucocorticoids, mineralcorticoids, and corticotropins. The chemical modifications of the present invention may be used to improve the solubility and dissolution rates of corticosteroids. Suitable corticosteroids for use in the present invention can be selected, for example, by their ability to demonstrate an anti-inflammatory effect as well as other useful pharmacological effects (e.g. anti-angiogenic) in treating ocular diseases by using in vivo retinal cell models. Exemplary corticosteroids of the present invention include, but are not limited to, triamcinolone, prednisolone, dexamethasone, fluocinolone acetonide, triamcinlone acetonide, hydrocortisone, methyprednisolone, betamethasone, beclomethasone, fludrocortisones, prednisone, and budesonide. By way of example, but not of limitation, budesonide is in clinical use for treatment of asthma, allergic rhinitis, and inflammatory bowel disease. It is a potent anti-inflammatory corticosteroid with a 1000 fold higher topical anti-inflammatory effect than cortisol. (1, 2). It is capable of reducing vascular epithelial grown factor (VEGF) secretion and mRNA expression in retinal pigment epithelia cells (ARPE19 cells) via glucocorticoid-receptor mediated mechanisms at nanomolar concentrations. Accordingly, budesonide is representative of a type of corticosteroid that may be useful in the context of the present invention for treating retinal ocular diseases.

The corticosteroid pro-drugs of the present invention contain modifications which increase the hydrophilicity of the corticosteroid. A pro-drug is generated by the attachment of one or more functional groups to the steroid backbone. The functional groups may be attached to the A, B, C, or D rings of the parent steroid backbone or to functional groups existing on the active corticosteroid. In one exemplary embodiment, the corticosteroid includes the introduction of at least one negatively charged terminal group to the parent compound. While not bound by the following theory, it is believed that the negatively charged terminal groups reduce binding of the corticosteroid to melanin and or other native eye components that result in the sequestration or removal of the corticosteroid from the eye. The negatively charged terminal acid may be bound to the parent compound by in vivo hydrolysable esters, amides, carbamates or other acceptable pro-drug linkages. In one exemplary embodiment, the functional groups are attached to the corticosteroid via ester linkages. In certain exemplary embodiments, the pro-drug functional group is attached to a terminal hydroxide present on the D ring or to an existing functional group attached thereto. In another exemplary embodiment, the pro-drug functional group is attached to a terminal hydroxy on a functional group attached to carbon 17 of the corticosteroid backbone. Functional groups that may be used to generate the corticosteroid pro-drugs of the present invention included sulphates, sulfphones, sulfoxides, sulphonic acids, citrates, phosphates, phosphines, phosphodiesters, phosphonic acids succinates, or salts thereof. In addition, functional groups that may be used in the present invention include the follower esters; maleate, citrate, tartrate, adipic acid, glutaric acid, malonic acid, and hydroxy succinic acid, hydroxy succinic acid esters. In one exemplary embodiment, the functional group is a sulphate or sulphate salt. In certain exemplary embodiments, the sulfate salt is an ammonium salt, such as, a sulfate triethylammonium salt. In another exemplary embodiment, the pro-drug functional group is a succinate or acid thereof.

In one exemplary embodiment, pro-drugs of the present invention have the following general formula:

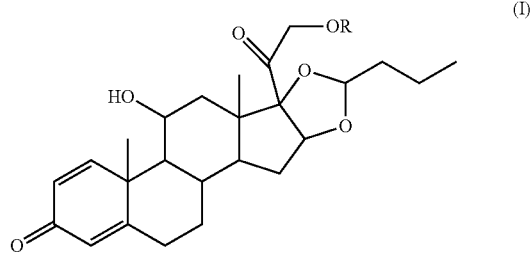
(I)

wherein R is any one of the R-groups listed in Table 1 below.

from low solubility and permeability of the eye. NSAIDs possess a number of pharmacological properties that may be useful in treating ocular diseases By way of example, but not of limitation, celecoxib is a potent and selective COX-2 inhibitor for use in the treatment of inflammatory diseases like rheumatoid arthritis and osteoarthritis. It has been shown previously that levels of prostaglandins increase in the diabetic retinas via COX-2 mediated processes (3,4). In addition, the levels of vascular endothelial growth factor (VEGF) mRNA and COX-2 expression in retinal pigment epithelial cells increase early in the course of diabetic retinopathy (5). Increased production of prostaglandins can also stimulate VEGF production in the retina (6). An increase in prostaglandin E2 (PGE2) and VEGF levels results in the breakdown of the blood-retinal-barrier leading to vascular linkage (7-9). Accordingly, NSAIDs with properties such as, but not limited to those of celecoxib, represent suitable NSAIDs for use in the context of the present invention for treatment of retinal ocular diseases. In one exemplary embodiment, the coxib is celecoxib. NSAIDs that may be used in the present invention include salicylates, propionic acid derivatives, acetic acid derivatives, enolic acid (oxicam) derivatives, fenamic acid derivatives (fenamates) and selective COX-2 inhibitors (coxibs). In one exemplary embodiment, the NSAID is a coxib. Exemplary coxibs include, but are not limited to, celecoxib, rofecoxib, valdecoxib, parecoxib, lumiracoxib, etoricoxib, and firocoxib. In one exemplary embodiment, the coxib is celecoxib. In another exemplary embodiment, the NSAID is diclofenac, ketoralac, nepafenac, or bromfenac. In another exemplary embodiment the COX-2 inhibitor is nimesulide.

The present invention comprises single and double pro-drugs of NSAIDs. The pro-drugs of the present invention comprise a NSAID with a terminal functional group containing a weak base to which a multi-functional counter acid is bound. In one exemplary embodiment, the weak base on the parent compound has a pKa value of approximately 7 to approximately 10. The multi-functional counter acid may be bound to the parent compound by in vivo hydrolysable esters, amides, carbamates or other acceptable pro-drug linkages. In one exemplary embodiment, the counter-acid is bound by an in vivo hydrolysable ester. While not bound by the following theory, it is believed that functional groups containing basic groups increase melanin binding. Melanin binding acts as a major barrier to effective distribution of a compound in an eye by sequestering or otherwise preventing

TABLE 1

Physicochemical properties of budesonide and prodrugs thereof

| Sl. No | Solute (Sol$_{aq}$; mg/ml; pH 7.4; 25° C.) | —R group | Mol. Wt. | Mol. Radius (nm) | Predicted[1] Log D (pH 7.4) | Predicted[1] Log P | Predicted[1] pK$_{a1}$, pK$_{a2}$ (acidic) | Predicted net mol. charge at pH 7.4 |
|---|---|---|---|---|---|---|---|---|
| 15 | Budesonide (0.02) | —H | 430.5 | 0.55 | 1.81 | 1.81 | 14.4, 15.7 | 0 |
| 16 | Adipic acid mono-budesonide ester | —COCH$_2$CH$_2$CH$_2$CH$_2$COOH | 558.7 | 0.60 | 0.4 | 2.71 | 4.6, 16.0 | 1– |
| 17 | Glutaric acid mono-budesonide ester | —COCH$_2$CH$_2$CH$_2$COOH | 544.5 | 0.60 | −0.15 | 2.37 | 4.5, 16.0 | 1– |
| 18 | Succinic acid mono-budesonide ester | —COCH$_2$CH$_2$COOH | 530.6 | 0.59 | −0.51 | 2.26 | 4.2, 16.05 | 1– |
| 19 | Malonic acid mono-budesonide ester | —COCH$_2$COOH | 516.5 | 0.59 | −1.71 | 1.92 | 3.1, 15.6 | 1– |
| 20 | Hydroxy succinic acid mono-budesonide ester | —COCH$_2$CH(OH)COOH | 546.5 | 0.60 | −2.0 | 1.75 | 3.16, 16.1 | 1– |
| 21 | Budesonide phosphate | —PO(OH)$_2$ | 510.5 | 0.59 | −3.7 | 1.04 | 1, 6.2, 16 | 2– |

Pro-Drugs of NSAIDs

NSAIDs are a class of drugs which includes members having eicosanoid-depressing and anti-inflammatory properties. Like corticosteroids members of the class can suffer the compound from reaching its target. Accordingly, modifications to the parent NSAID compound that can reduce melanin binding are contemplated by the present invention. As used herein, "a multi-functional compound or counter acid" is a molecule containing multiple functional groups. For example a multi-functional group can be a compound with a carbon backbone to which multiple functional groups are attached or single molecules such as phosphates and sulfates. Suitable multi-functional counter acids for use in the present invention include, but are not limited to, aspartates, maleates, fumarates, tartarates, citrates, amides and succinates. Exemplary amides that may be used in the present invention include ethyl butyramide, privaloylamide, butyamide, propionamide, acetamide, sinapamide, salicyl-

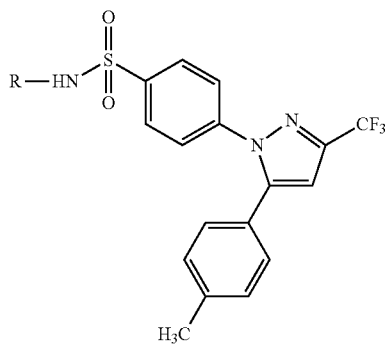

(II)

wherein R is any one of the R-groups listed in Table 2 below.

TABLE 2

Physicochemical properties of cetecoxib/prodrugs selected for transscleral transport studies

| Sl. No | Solute ($Sol_{aq}$; mg/ml; pH 7.4; 25° C.) | —R group | Mol. Wt. | Mol. Radius (nm) | Predicted[1] Log D (pH 7.4) | Predicted[1] Log P | Predicted[1] $pK_{a1}$, $pK_{a2}$ (acidic) | Predicted net mol. charge at pH 7.4 |
|---|---|---|---|---|---|---|---|---|
| 1 | Celecoxib (0.005) | —H | 381 | 0.53 | 3.32 | 3.35 | 8.8, 8.8 | 0 |
| 2 | Methyl-ethanolamine mannich base of celecoxib | —$CH_2N(CH_3)CH_2CH_2OH$ | 468 | 0.57 | 3.01 | 3.08 | 8.57 | 0 |
| 3 | Celecoxib ethyl butyramide | —$COCH(CH_2CH_3)_2$ | 479 | 0.57 | 2.5 | 4.4 | 5.04 | 0 |
| 4 | Celecoxib pivaloylamide | —$COC(CH_3)_3$ | 465 | 0.57 | 1.9 | 3 8 | 5.04 | 0 |
| 5 | Celecoxib butyramide | —$COCH_2CH_2CH_3$ | 463 | 0.57 | 1.7 | 3.95 | 4.8 | 0 |
| 6 | Celecoxib propionamide | —$COCH_2CH_3$ | 449 | 0.57 | 1.5 | 3.75 | 4.74 | 0 |
| 7 | Celecoxib-acetamide | —$COCH_3$ | 423 | 0.55 | 1.2 | 2.98 | 5.0 | 0 |
| 8 | Celecoxib sinapamide | —$COCH=CHC_6H_2(4-OH)2,5-(OCH_3)_2$ | 587 | 0.02 | 1.0 | 3.0 | 5.04, 8.49 | 1− |
| 9 | Celecoxib 4-amino salicylamide | —$COC_6H_3(OH)(NH_2)$ | 516 | 0.59 | 0.75 | 2.76 | 5 04, 9.08 | 1+ |
| 10 | Celecoxib bis(hydroxymethyl)butyramide | —$COC(CH_2OH)_2CH_2CH_3$ | 512 | 0.59 | 0.6 | 2.6 | 5.04, 13.9 | 0 |
| 11 | Celecoxib octenyl succinamidic acid | —$COCH_2CH(C_8H_{15})COOH$ | 605 | 0.63 | −0.04 | 4.8 | 4.4, 4.8 | 1− |
| 12 | Celecoxib gycinamide | —$COCH_2NH_2$ | 438.5 | 0.56 | −0.4 | 2.1 | 4.74 | 1+ |
| 13 | Celecoxib adipamidic acid | —$COCH_2CH_2CH_2CH_2COOH$ | 509 | 0.59 | −1.1 | 3.1 | 4.73, 5.04 | 1− |
| 14 | Celecoxib glutaramidic acid | —$COCH_2CH_2CH_2COOH$ | 495 | 0.58 | −1.95 | 2.76 | 4.54, 4.74 | 1− |
| 15 | Celecoxib succinamidic acid (1.0) | —$COCH_2CH_2COOH$ | 481 | 0.57 | −4.8 | 2.53 | 4.4, 5.0 | 1− |
| 16 | Celecoxib-maleiamidic acid | —$COCH=CHCOOH$ | 479 | 0.57 | −6.1 | 2.6 | 2.3, 4.3, 4.7 | 1− |
| 17 | Celecoxib malonamidic acid | —$COCH_2COOH$ | 467 | 0.57 | −3.86 | 2.4 | 2.98, 4.74 | 1− |
| 18 | Celecoxib ethyl succinamide | —$COCH_2CH_2COOCH_2CH_3$ | 509 | 0.59 | 1.34 | 3.0 | 4.74 | 0 |
| 19 | Celecoxib ethyl maleiamidede | —$COCH=CHCOOCH_2CH_3$ | 507 | 0.59 | 1.45 | 3.71 | 4.74 | 0 |
| 20 | Celecoxib-N,N-dimethyl-aspartamidic acid | —$COCH\{N(CH_3)_2\}CH_2COOH$ | 524 | 0.59 | −2.84 | 3.06 | 2.7, 5.0 | 1− |
| 21 | Celecoxib-ethoxysuccinamidic acid | —$COCH_2CH(OCH_2CH_3)COOH$ | 525 | 0.59 | −3.33 | 2.62 | 3.8, 5.0 | 1− |
| 22 | Celecoxib-hydroxysuccinamidic acid | —$COCH_2CH(OH)COOH$ | 497 | 0.58 | −3.82 | 2.66 | 3.9, 5.0 | 1− |
| 23 | Celecoxib-aspartamidic acid | —$COCH(NH_2)CH_2COOH$ | 496 | 0.58 | −3.97 | 1.63 | 3.3, 5.0 | 0 | amide, a succinamide, sinapamide, and a gycinamide. In one exemplary embodiment, the multi-functional counter ion is a succinate or acid thereof.

Figure 8:
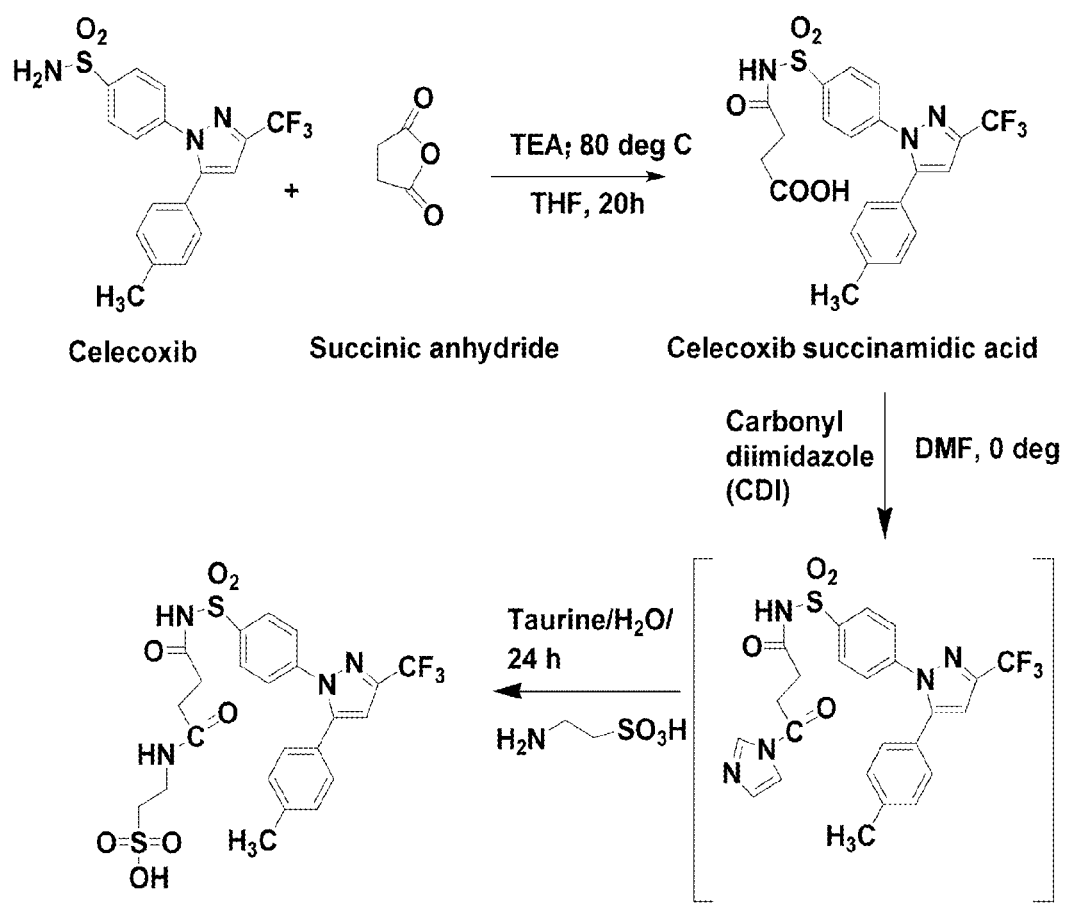
FIG. 8 is a schematic of a synthetic pathway for single pro-drug (celecoxib succinamidic acid, C-SA) and double pro-drug (celecoxib succinamidic acid taurine, C-SA-T) of celecoxib.

In one exemplary embodiment the pro-drug of the present invention is a celecoxib modified to mask a terminal sulfonamide group (predicted pKa value of 8.8) with a succinic anhydride to form a celecoxib succinamidic acid. A synthetic pathway for generating a celecoxib succinamidic acid is shown in FIG. 8 and described in further detail in the Examples section below.

In another exemplary embodiment, the pro-drug of the present invention has the following general formula:

In yet another exemplary embodiment, the pro-drug of the present invention has the following general formula:

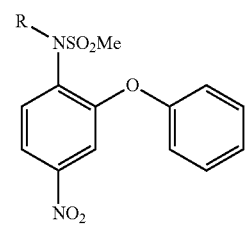

(III)

where R is one of the R-groups listed in Table 3 below.

TABLE 3

Physicochemical properties of nimesulide and prodrugs thereof

| Sl. No | Solute (Sol$_{aq}$; mg/ml; pH 7.4; 25° C.) | —R group | Mol. Wt. | Mol. Radius (nm) | Predicted[1] Log D (pH 7.4) | Predicted[1] Log P | Predicted[1] pK$_{a1}$, pK$_{a2}$ (acidic) | Predicted net mol. charge at pH 7.4 |
|---|---|---|---|---|---|---|---|---|
| 1 | Nimesulide (0.007) | —H | 308.3 | 0.50 | 3.8 | 3.8 | 8.5 | 0 |
| 2 | Nimesulide acetamide | —COCH$_3$ | 350.9 | 0.52 | 2.36 | 2.36 | none | 0 |
| 3 | Nimesulide glycinamide | —COCH$_2$NH$_2$ | 365.07 | 0.52 | 1.16 | 1.16 | 6.52 | 1+ |
| 4 | Nimesulide adipamidic acid | —COCH$_2$CH$_2$CH$_2$CH$_2$COOH | 436.4 | 0.56 | −0.22 | 2.0 | 4.73 | 1− |
| 5 | Nimesulide glutaramidic acid | —COCH$_2$CH$_2$CH$_2$COOH | 422 | 0.55 | −0.7 | 2.26 | 4.5 | 1− |
| 6 | Nimesulide N,N-dimethyl aspartamidic acid | —COCHN(CH$_3$)$_2$CH$_2$COOH | 451.5 | 0.56 | −1.7 | 1.32 | 2.71 | 1− |
| 7 | Nimesulide malonamidic acid | —COCH$_2$COOH | 394.5 | 0.54 | −2.46 | 1.52 | 2.06 | 1− |
| 8 | Nimesulide succinamidic acid | —COCH$_2$CH$_2$COOH | 408.4 | 0.54 | −4.3 | 1.4 | 4.04, 4.15 | 1− |

In certain exemplary embodiments, the NSAID pro-drugs of the present invention further comprise the addition of a taurine to form a double pro-dug compound. Taurine is accumulated into photoreceptor cells and to a certain extent Muller, amacrine and bipolar cells (10-13). In addition, taurine has been reported to penetrate through the blood-retinal-barrier into the retina. Supplementation with taurine has been documented to reduce the up-regulation of VEGF expression in a streptozotocin-induced diabetic retinopathy rat model (14). The zwitter ionic nature of taurine is believed to hinder its passive diffusion through lipid membranes. The observed retinal influx clearance of taurine was found to be significantly higher than those of non-permeable paracellular markers, indicating a carrier-mediated rather than diffusion mediated process.

In one exemplary embodiment, the taurine is bound to a terminal functional group on the multi-functional counter acid. In another exemplary embodiment, the taurine is bound directly to the NSAID parent compound. In yet another exemplary embodiment, more than one taurine may be bound to the multi-functional counter acid, the parent compound, or a combination thereof. Similar concepts can be applied to other drugs including corticosteroids. In one exemplary embodiment taurine is bound to a celcoxib pro-drug of the present invention. In another exemplary embodiment, the taurine is bound to a celecoxib succinamidic acid pro-drug. A synthetic pathway for binding taurine to a celecoxib succinamidic acid is shown in FIG. 8 and described in further detail in the Examples section below.

Ruboxistaurin Pro-Drugs

The present invention comprises single and double pro-drugs of ruboxistaurin. Ruboxistaurin is a protein kinase C beta inhibitor the overexpression of which has been implicated in the development of diabetic retinopathy. In one exemplary embodiment, the pro-drug of the present invention has the following general formula:

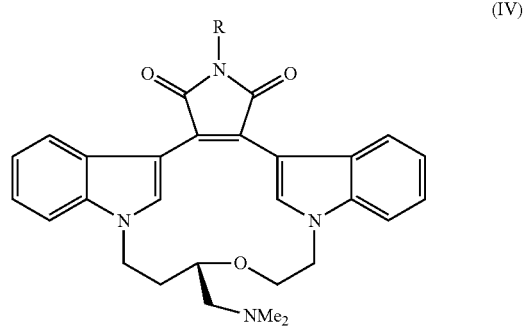

(IV)

wherein R is aspartates, maleates, fumarates, tartarates, citrates, amides, succinates, or ester or amidic acids thereof. In one exemplary embodiment, R is any one of the R-groups listed in Table 4 below.

TABLE 4

Physicochemical properties of p ruboxistaurin and prodrugs thereof

| Sl. No | Solute (Sol$_{aq}$; mg/ml; pH 7.4; 25° C.) | —R group | Mol. Wt. | Mol. Radius (nm) | Predicted[1] Log D (pH 7.4) | Predicted[1] Log P | Predicted[1] pK$_{a1}$, pK$_{a2}$ (acidic) | Predicted net mol. charge at pH 7.4 |
|---|---|---|---|---|---|---|---|---|
| 9 | Ruboxistaurin (0.029) | —H | 488.5 | 0.57 | 2.2 | 3.9 | 8.26 | 0 |
| 10 | Ruboxistaurin acetamide | —COCH$_3$ | 512.66 | 0.59 | 1.7 | 3.2 | none | 0 |
| 11 | Ruboxistaurin adipamidic acid | —COCH$_2$CH$_2$CH$_2$CH$_2$COOH | 582.7 | 0.61 | 0.35 | 3.1 | 4.7 | 1− |
| 12 | Ruboxistaurin giutaramidic acid | —COCH$_2$CH$_2$CH$_2$COOH | 568 | 0.60 | −0.9 | 2.21 | 4.57 | 1− |
| 13 | Ruboxistaurin malonamidic acid | —COCH$_2$COOH | 540 | 0.60 | −1.25 | 1.77 | 2.45 | 1− |
| 14 | Ruboxistaurin succinamidic acid | —COCH$_2$CH$_2$COOH | 554.6 | 0.60 | −2.8 | 2.8 | 4.21, 4.31 | 1− |

In certain exemplary embodiments, the ruboxistaurin pro-drugs of the present invention further comprise the addition of a taurine to form a double pro-dug compound. In one exemplary embodiment, the taurine is bound to a terminal functional group on the R-group. In another exemplary embodiment, the taurine is bound directly to the ruboxistaurin parent compound. In yet another exemplary embodiment, more than one taurine may be bound to the R-group, the parent compound, or a combination thereof.

Pharmaceutical Compositions

The corticosteroid and NSAID pro-drug compounds described herein can be provided as physiologically acceptable formulations using known techniques, and the formulations can be administered by standard routes including but not limited to topical, periocular or transscleral, suprachoroidal, subretinal, intravitreal and systemic routes. 100% pure isomers are contemplated by this invention; however a stereochemical isomer (labeled as α or β, or as R or S) may be a mixture of both in any ratio, where it is chemically possible by one skilled in the art. Also contemplated by this invention are both classical and non-classical bioisosteric atom and substituent replacements, such as are described by Patani and Lavoie ("Bio-isosterism: a rational approach in drug design" Chem. Rev. (1996) p. 3147-3176) and are well known to one skilled in the art. Such bioisosteric replacements include, for example, but are not limited to, substitution of a S or a NH for an O.

The formulations in accordance with the present invention can be administered in the form of a tablet, a capsule, a lozenge, a cachet, a solution, a suspension, an emulsion, a powder, an aerosol, a suppository, a spray, a pastille, an ointment, a cream, a paste, a foam, a gel, a tampon, a pessary, a granule, a bolus, a mouthwash, an eye drop or a transdermal patch.

The formulations include those suitable for oral, rectal, nasal, inhalation, topical (including dermal, transdermal, buccal, and eye drops), vaginal, parenteral (including subcutaneous, intramuscular, intravenous, intradermal, intraocular (including local injections such periocular, suprachoroidal, subretinal, and intravitreal), intratracheal, and epidural) or inhalation administration. In one exemplary embodiment, the corticosteroid pro-drugs of the present invention are formulated for transcleral delivery. Transcleral delivery includes subconjunctival, subtenons', and retrobulbar trancleral delivery. In one exemplary embodiment, the NSAID pro-drugs are formulated for administration topically as eye drops. The formulations can conveniently be presented in unit dosage form and can be prepared by conventional pharmaceutical techniques. Such techniques include the step of bringing into association the active ingredient and a pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tablets may be made by molding, in a suitable machine, a mixture of the powdered compound moistened with an inert liquid diluent. The tablets may optionally be coated or scored and may be formulated so as to provide a slow or controlled release of the active ingredient therein.

Formulations suitable for topical administration in the mouth include lozenges comprising the ingredients in a flavored base, usually sucrose and acacia or tragacanth; pastilles comprising the active ingredient in an inert base such as gelatin and glycerin, or sucrose and acacia; and mouthwashes comprising the ingredient to be administered in a suitable liquid carrier.

Formulations suitable for topical administration to the skin may be presented as ointments, creams, gels, pastes, and eye drops comprising the ingredient to be administered in a pharmaceutical acceptable carrier.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is taken; i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing, in addition to the active ingredient, ingredients such as carriers as are known in the art to be appropriate.

Formulation suitable for inhalation may be presented as mists, dusts, powders or spray formulations containing, in addition to the active ingredient, ingredients such as carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. Formulations suitable for parenteral administration also include, but are not limited to, nanoparticle formulations made by numerous methods as disclosed in U.S. patent application Ser. No. 10/392,403 (Publication No. US 2004/0033267), U.S. patent application Ser. No. 10/412,669 (Publication No. US 2003/0219490), U.S. Pat. No. 5,494,683, U.S. patent application Ser. No. 10/878,623 (Publication No. U.S. Pat. No. 2005/0008707), U.S. Pat. Nos. 5,510,118, 5,524,270, 5,145,684, 5,399,363, 5,518,187, 5,862,999, 5,718,388, and 6,267,989, all of which are hereby incorporated herein by reference in there entirety. A review of drug formulation technology is provided in "Water Insoluble Drug Formulation" by Rong Liu, editor, pp. 1-633, (2000) CRC Press LLC, which is incorporated herein by reference in its entirety.

It should be understood that, in addition to the ingredients particularly mentioned above, the formulations of the present invention may include other agents conventional in the art having regard to the type of formulation in question, for example, those suitable for oral administration may include flavoring agents, and nanoparticle formulations (e.g.; less than 2000 nanometers, preferably less than 1000 nanometers, most preferably less than 500 nanometers in average cross section) may include one or more than one excipient chosen to prevent particle agglomeration.

Retinal Ocular Diseases and Methods of Use

The corticosteroid, NSAID, and ruboxistaurin single and double pro-drug formulations of the present invention may be used to treat diseases effecting the posterior segment of the eye. For ease of reference the single and double pro-drug formulations of the present invention are referred to collectively below as the pro-drug formulation. Diseases affecting the posterior segment of the eye that may be treated with the corticosteroid and NSAID pro-drug compounds of the present invention include degenerative, vascular, inflammatory, and infectious diseases affecting the posterior segment of the eye. Exemplary degenerative diseases include, but are not limited to, ARMD, and retinitis pigmentosa. Exemplary vascular diseases include, but are not limited to, diabetic retinopathy and choroidal neovascularization. Exemplary inflammatory diseases include, but are not limited to uveitis. Exemplary infectious diseases include, but are not limited to CMV retinitis. In addition, the corticosteroid and NSAID pro-drug compounds of the present invention may used to treat glaucoma and optic neuritis.

In one exemplary embodiment, the present invention comprises administering to a patient with a disease affecting the posterior segment of the eye a composition comprising a corticosteroid pro-drug of the present invention, a NSAID pro-drug of the present invention, a ruboxistaurin pro-drug or a combination thereof. In one exemplary embodiment the corticosteroid pro-drug is delivered transclerally. In another exemplary, embodiment, the NSAID pro-drug is administered to the eye topically in the form of eye drops. In another exemplary embodiment, the corticosteroid pro-drug, NSAID pro-drug, ruboxistaurin pro-drug or a combination thereof are implanted or systemically administered in an extended release formulation. In one exemplary embodiment, the extended release formulation is a nanoparticle in porous microparticle (NPinPMP) formulation according to the present invention and described in greater detail below.

In another exemplary embodiment, the present invention comprises methods reducing blood retinal barrier leakage comprising administering to a patient in need thereof a composition comprising a corticosteroid pro-drug of the present invention, a NSAID pro-drug, a ruboxistaurin pro-drug of the present invention, or a combination thereof. In one exemplary embodiment the corticosteroid pro-drug is delivered transclerally. In another exemplary, embodiment, the NSAID pro-drug is administered to the eye topically in the form of eye drops. In another exemplary embodiment, the corticosteroid pro-drug, NSAID pro-drug, ruboxistaurin pro-drug or a combination of both are implanted or systemically administered in an extended release formulation. In one exemplary embodiment, the extended release formulation is a nanoparticle in porous microparticle formulation according to the present invention and described in greater detail below.

In another exemplary embodiment, the present invention comprises methods of reducing retinal leukostasis comprising administering to a patient in need thereof a composition comprising a corticosteroid pro-drug of the present invention, a NSAID pro-drug of the present invention, a ruboxistaurin pro-drug, or a combination thereof. In one exemplary embodiment the corticosteroid pro-drug is delivered transclerally. In another exemplary, embodiment, the NSAID pro-drug is administered to the eye topically in the form of eye drops. In another exemplary embodiment, the corticosteroid pro-drug, NSAID pro-drug, or a combination of both are implanted or systemically administered in an extended release formulation. In one exemplary embodiment, the extended release formulation is a nanoparticle in porous microparticle formulation according to the present invention and described in greater detail below.

In another exemplary embodiment, the present invention comprises methods of reducing PGE2 levels in a posterior segment of the eye comprising administering to a patient in need thereof a composition comprising a corticosteroid pro-drug of the present invention, a NSAID pro-drug of the present invention, a ruboxistaurin pro-drug, or a combination thereof. In one exemplary embodiment the corticosteroid pro-drug is delivered transclerally. In another exemplary, embodiment, the NSAID pro-drug is administered to the eye topically in the form of eye drops. In another exemplary embodiment, the corticosteroid pro-drug, NSAID pro-drug, ruboxistaurin pro-drug or a combination of both are implanted or systemically administered in an extended release formulation. In one exemplary embodiment, the extended release formulation is a nanoparticle in porous microparticle formulation according to the present invention and described in greater detail below. As used herein reduction of PGE2 levels includes a reduction in regulatory components involved in the biosynthesis of PGE2 levels as well as physical PGE2 levels itself. A reduction in PGE2 levels is based on levels bellowed those observed in comparable healthy tissues. In one exemplary embodiment, methods of the present invention result in a reduction of at least about 5%, 10%, 15%, 20%, 25%, 30%, 35%, 40%, 45%, %50, 55%, 60%, 65%, 70%, 75%, 80%, 85%, 90%, 95%, or 100% of PGE2 levels below that observed in comparable healthy tissue.

In another exemplary embodiment, the present invention comprises methods of reducing VEGF levels in a posterior segment of the eye comprising administering to a patient in need thereof a composition comprising a corticosteroid pro-drug of the present invention, a NSAID pro-drug of the present invention, a ruboxistaurin pro-drug, or a combination thereof. In one exemplary embodiment the corticosteroid pro-drug is delivered transclerally. In another exemplary, embodiment, the NSAID pro-drug is administered to the eye topically in the form of eye drops. In another exemplary embodiment, the corticosteroid pro-drug, NSAID pro-drug, ruboxistaurin pro-drug or a combination of both are implanted or systemically administered in an extended release formulation. In one exemplary embodiment, the extended release formulation is a nanoparticle in porous microparticle formulation according to the present invention and described in greater detail below. As used herein reduction of VEGF levels includes a reduction mRNA and/or protein levels of VEGF as well as in regulatory components involved in the transcription and translation of VEGF. A reduction in VEGF levels is based on levels bellowed those observed in comparable healthy tissues. In one exemplary embodiment, methods of the present invention result in a reduction of at least about 5%, 10%, 15%, 20%, 25%, 30%, 35%, 40%, 45%, %50, 55%, 60%, 65%, 70%, 75%, 80%, 85%, 90%, 95%, or 100% of PGE2 levels below that observed in comparable healthy tissue.

Particle-in-Particle Extended Release Formulations

In another aspect the present invention is directed to particle-in-particle (PinP) extended release compositions. The extended release compositions of the present invention comprise an inner particle contained within a larger porous outer particle, including various architectures such as a nanoparticle in porous microparticle (NPinPMP), small nanoparticle in porous large nanoparticle (SNPinPLNP), and small microparticle in porous large microparticle (SMPin-PLMP). The inner particle is smaller and relatively non-expandable as compared to the larger outer particle during processing. The outer particle is expandable and forms a significantly porous structure during processing that allows the embedding of the inner particle within the outer particle's porous structure.

As used in the context of the present invention, a particle is considered to expand in the presence of a supercritical fluid if the particle's initial surface area increases within a range of approximately 1.25 to approximately 100 times. In certain exemplary embodiments, the particle is considered to expand if the particle's initial surface surface area expands within a range of approximately 1.25 to approximately 5 times, approximately 5 to approximately 25 times, approximately 25 to approximately 50 times, approximately 50 to approximately 75 times, or approximately 75 to 100 times. Alternatively, a particle is considered to expand if the particle's initial size increases by at least 5%, 10%, 15%, 20%, 25%, 30%, 35%, 40%, 45%, or 50%.

Inner particles of the present invention are made using polymeric or non-polymeric materials that do not expand in the presence of a supercritical fluid. In certain exemplary embodiments, the nanoparticle material is a polymeric material that will not expand in the presence of supercritical fluids. In certain exemplary embodiments, the polymeric material is a material that will not expand in the presence of supercritical carbon dioxide. Examples of suitable polymeric and non-polymeric materials that may be used in the present invention include polylactide (PLA), poly(glycolic acid), co-polymers of lactic and glycolic acid (PLGA), cellulose derivatives, chitosan, polyethylene (PE), polypropylene, poly(tetrafluoroethylene), poly(ethylene terephathalate), iron oxide, cerium oxide, zinc oxide, gold, silver, other biocompatible metals and crystals, and silica. Crystalline materials or those with large crystalline regions are less likely to expand during supercritical fluid processing. Polymeric inner particles may be prepared using conventional emulsion-solvent evaporation methods or other similarly suitable synthesis methods. Therapeutic agents may be encapsulated in the inner particles during formation or loaded on the surface after formation of the inner particles.

Outer particles of the present invention are made using materials that expand in the presence of a supercritical fluid. In certain exemplary embodiments, the microparticle material is a polymeric material that expands in the presence of a supercritical fluid. In certain exemplary embodiments, the material that expands in the presence of supercritical carbon dioxide. Examples of suitable polymeric materials that may be used in the present invention include lactide-co-glycolide, polyamides, polycarbonates, polyakylene glycols, polyalkylene oxides, polyvinyl alcohols, polyvinyl ethers, polyvinly esters, polyvinylpyrrolidone, polyglycolides, and co-polymers thereof. In addition, suitable polymer materials also include alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose acetate butyrate, cellulose acetate phthalate, carboxylethyl cellulose, cellulose poly(methyl methacrylate), poly(elthylmethacrylate), poly(butymethacrylate), poly(vinyl alcohols), poly(vinyl acetate), and polyvinylpryrrolidone. In general, amorphous materials or those with large amorphous regions are suitable for expansion during supercritical fluid processing. Polymeric outer particles may be prepared using conventional emulsion-solvent evaporation, or other similarly suitable synthesis methods. In certain exemplary embodiments, therapeutic agents may be encapsulated in the outer particles during formation or loaded on the surface after formation of the outer particles.

The extended release compositions may be used to deliver a wide range of therapeutic agents where an extended release profile is desired. The process of generating various particle architectures is achieved using supercritical fluid flow technology. The resulting organic solvent-free loading is especially well suited to drugs, such as peptide and nucleotide based drugs, and viral vectors, which are susceptible to aggregation or degradation. A therapeutic agent may be loaded on the surface of the inner particle, the outer particle or both; in the matrix of the inner particle, outer particle or both; present in the pores of the outer particle; or a combination thereof. In certain exemplary embodiments, therapeutic agents may be present on the surface of the inner particle. In another exemplary embodiment, therapeutic agents may be present on the surface of the inner and outer particle. In yet another exemplary embodiment, therapeutic agents may be present in the matrix of the inner particle. In another exemplary embodiment, a therapeutic agent may be present in the matrix of both the inner and outer particle. In another exemplary embodiment, a therapeutic agent may further be present in the porous structure of the outer particle.

Therapeutic agents that may be loaded on the nanoparticles include small-molecule-based therapeutic agents, nucleic acid-based therapeutic agents, viral vectors, and peptide based therapeutic agents. In one exemplary embodiment, the therapeutic agent is a peptide based therapeutic agent. The terms "peptide," "polypeptide" and "protein" are used interchangeably herein. Unless otherwise noted, the terms refer to a polymer having at least two amino acids linked through peptide bounds. The terms thus include oligopeptides, protein fragments, analogs, derivatives, glycosylated derivatives, pegylated derivatives, fusion proteins and the like. In another exemplary embodiment, the therapeutic agent is a corticosteroid pro-drug NSAID pro-drug, a ruboxistaurin pro-drug of the present invention, or a combination thereof. In certain exemplary embodiments, therapeutic loaded inner or outer particles are lyophilized.

Inner and outer particles are admixed together and exposed to a supercritical fluid under high pressure. In certain exemplary embodiments, the supercritical fluid is carbon dioxide. Upon exposure to the supercritical fluid the outer particles expand to create a porous structure on the outer surface. The supercritical fluid then infuses the inner particles into the outer particles to form particle-in-particle extended release formulations. In one exemplary embodiment, the particle-in-particle extended release formulations comprise the incorporation of inner nanoparticles having a diameter of approximately 1 nm to approximately 900 nm in an outer microparticle having a diameter of approximately 1 µm to approximately 100 µm. In another exemplary embodiment, the particle-in-particle extended release formulations comprise the incorporation of an inner nanoparticle having a diameter of approximately 1 nm to approximately 300 nm in an outer nanoparticle having a diameter of approximately 10 nm to approximately 999 nm. In yet another exemplary embodiment, the particle-in-particle extended release formulations include the incorporation of an inner microparticle having a diameter of approximately 1 µm to approximately 100 µm in an outer microparticle having a diameter of approximately 2 µm to approximately 500 µm. Selection of an appropriate sized inner and outer particle will depend on the type of material comprising the particles, the expansive ability of the outer partical in the supercritical fluid used, and the size of inner particles to be incorporated within the outer particle. These are all factors that can be readily selected for by one of ordinary skill in the art. In general, the size ratio between the inner and outer particle may vary from approximately 1:2 to approximately 1:100. In one exemplary embodiment the size ratio may be 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, or 1:100

Formation of NPinPMPs may be achieved by exposure of the nanoparticles and microparticles at approximately psi to approximately 1000 psi to approximately 1400 psi. The time of exposure may vary from approximately 5 minutes to approximately 2 hours. The temperature may range from 30° C. to 45° C. The selection of an appropriate pressure and temperature range are determined primarily by the range of temperature and pressures near the supercritical point for a given supercritical fluid. Accordingly, one of ordinary skill in the art will be able to select the appropriate time, temperature, and pressure ranged based upon the supercritical fluid used, the size or amount of outer particle expansion desired, and the degree of porosity in the outer particle desired. For example, exposure for longer periods of time and/or at higher pressures followed by pressure quench will result in greater expansion and porosity than shorter exposure times and/or pressures.

In one exemplary embodiment, the inner particles and outer particles are mixed at a ratio of approximately 1:3. In one exemplary embodiment, the ratio of inner particles to outer particles used is approximately 1:9. These ratios will influence the extent of nanoparticle incorporation and slow release of the drug. In general, the larger the amount of inner particles relative to outer particles the higher the amount of inner particles incorporated in outer particle, increasing the drug release rates and the dose. The smaller the amount of inner particles relative to the outer particles, the smaller the burst release.

The compositions and methods are further illustrated by the following non-limiting examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention.

EXAMPLES

Example 1.1

Materials

Budesonide was purchased from Spectrum Chemical and Laboratory Products, a division of Spectrum Chemical Mfg. Corp. (New Brunswick, N.J., USA). Benzene, pyridine, triethylamine, sulfatrioxide triethylamine complex, and succinic anhydride were purchased from Sigma-Aldrich (St. Louis. Mo., USA). High performance liquid chromatography (HPLC) grade acetonitrile and methanol were purchased from Fisher Scientific (Philadelphia, Pa., USA). Freshly excised bovine eyes were purchased from G & C Meat Company, Colorado Springs, Colo., USA.

Synthesis of Budesonide Sulfate

To a solution of budesonide (50 mg; 0.116 mmoles) in 1 ml of anhydrous benzene and pyridine (1:1), was added sulfatrioxide triethylamine complex (STT; 53.2 mg; 0.29 mmoles) in portions with stirring at 55-60° C. for 60 min (FIG. 1). The formation of product was monitored every 10 min with the help of TLC using chloroform-methanol (80-20) as mobile phase. After 1 h, the reaction mixture was evaporated for 2 h under reduced pressure to remove the solvent (benzene, B.P. 80° C.; pyridine, B.P. 116° C.) and a mixture of budesonide, budesonide-21-sulfate triethylammonium salt and STT was obtained as oily residue. This mixture was subjected to silica-gel open-column chromatography and further purified by preparative thin layer chromatogarphy. Chloroform:methanol was used as the mobile phase for product separation by chromatography. Product formation was confirmed by LC-MS/MS and NMR analysis.

Synthesis of Budesonide Succinate 100 mg of budesonide (0.2322 mmoles) was dissolved in 1 ml of anhydrous pyridine. 116 mg of succinic anhydride (1.16 mmoles) was added to the above solution (FIG. 1). The reaction mixture was stirred at room temperature for 18 h. There was slight formation of product as indicated by TLC. The reaction temperature was then raised to 50° C. and allowed to stir for another 6 h. TLC and LC-MS/MS showed the formation of product. The reaction mixture was added dropwise in 2 g ice+2 ml of water+1 ml of HCl in a beaker placed in an ice bath. The precipitated product was collected by suction filtration. The solid was kept overnight for drying under vacuum in a dessicator. Product formation was confirmed by LC-MS/MS and NMR analysis.

Solubility Determination of Pro-Drugs

Solubility of budesonide succinate was determined in phosphate buffered saline (PBS; pH 7.4) at 25° C. after adding the pro-drug at a concentration of 1 mg/ml. At the end of 24 h, the suspension was centrifuged at 15,000 rpm for 15 minutes at 4° C. using accuSpin Micro17 (Fisher Scientific, USA). The pro-drug concentration in the supernatant after filtration through 0.2 μm filter was determined using LC-MS/MS.

Solubility of budesonide succinate was determined in phosphate buffered saline (PBS; pH 7.4) at 25° C. after adding the pro-drug at a concentration of 1 mg/ml. At the end of 24 h, the suspension was centrifuged at 15,000 rpm for 15 minutes at 4° C. using accuSpin Micro17 (Fisher Scientific, USA). The pro-drug concentration in the supernatant after filtration through 0.2 μm filter was determined using LC-MS/MS.

Tissue Isolation from the Bovine Eye

Freshly excised bovine eyes were used in all studies. For isolation of sclera and choroid-RPE (CRPE) (28), the anterior segment of the eye was removed with a circumferential cut below the limbus. The eye was cut into two halves along the geometric axis, a line joining the anterior pole (corneal center) and the posterior pole (center of the scleral curve), and the vitreous was removed. Neural retina was removed by exposing the eyecup to isotonic assay buffer at pH 7.4. Equatorial region of the remaining sclera-choroid-RPE (SCRPE) was used as is for SCRPE transport studies.

In Vitro Transccleral Transport of Budesonide/Budesonide Pro-Drugs

Bovine sclera and sclera-choroid-RPE transport study was conducted as described previously (28-30). Isotonic assay buffer (pH 7.4) with the following composition was used during the entire tissue isolation procedure and transport study: NaCl (122 mM), NaHCO$_3$ (25 mM), MgSO$_4$ (1.2 mM), K$_2$HPO$_4$ (0.4 mM), CaCl$_2$ (1.4 mM), HEPES (10 mM), and glucose (10 mM). After mounting the tissues in modified Using chambers, donor solution (1.5 ml of 0.05 mM drug/prodrug) was filled in chambers facing the episcleral side and receiver chambers were filled with the assay buffer (pH 7.4) for A to B and vice-versa for B to A transport studies. p-amino hippuric acid (0.5 mM) was added in the transport study of budesonide succinate from A to B. The transport study was conducted for 6 h at 37° C. under 95% air and 5% $CO_2$ aeration. Two hundred microliters of sample was collected from the receiver side at specific time intervals and replenished with fresh buffer. The drug/pro-drug content in the receiver and donor samples was analyzed using an LC-MS/MS method.

Pharmacokinetic Model Development

Pharmacokinetic model was developed for three sets of budesonide succinate transport studies: A to B (sclera to RPE, FIG. 3A), A to B+MCT inhibitor (sclera to RPE, FIG. 4A) and B to A (RPE to sclera, FIG. 5A). The model was developed in such a way that it accounted for transport of pro-drug from the donor to the receiver side, transport of parent drug formed in the donor chamber to the receiver side over the period of transport study, loss of pro-drug/drug into the tissues and any backward transport from the receiver to the donor side. The transport rate constants for parent drug and pro-drug were calculated from the cumulative percentage transport values. Rate constant for conversion of pro-drug to the parent drug was calculated from the percentage of the pro-drug and parent drug formed. Model was run with the dose amounts observed in the donor and receiver sides after 6 h transport studies. Final best fit model was run by DAMPING-GAUSS/SIMPLEX fitting algorithm, Fehlberg RFK 45 numerical integration method and equal weights for weighting of prodrug as well as parent drug transport.

Results

The final yields of the purified products were ~50% (FIG. 1). Budesonide sulfate formation was checked by LC-MS/MS (−Q1: m/z=509) and $^1$HNMR ($D_2O$, downfield shift of two protons on C 21 by 0.5 ppm after introduction of sulfate group). Similarly, budesonide succinate formation was also confirmed by LC-MS/MS (−Q1: m/z=429) and $^1$HNMR ($CDCl_3$), chemical shift values (δ, ppm) were as follows: 0.960 (s, 3H), 1.5 (s, 3H), 2.9 (t, 4H, succinate protons), 6.0 (s, 1H), 6.31 (d, 1H), 7.1 (d, 1H).

Solubility of budesonide succinate was found to be 51±3 μg/ml in phosphate buffered saline (pH 7.4) at 25° C.

Figure 2:
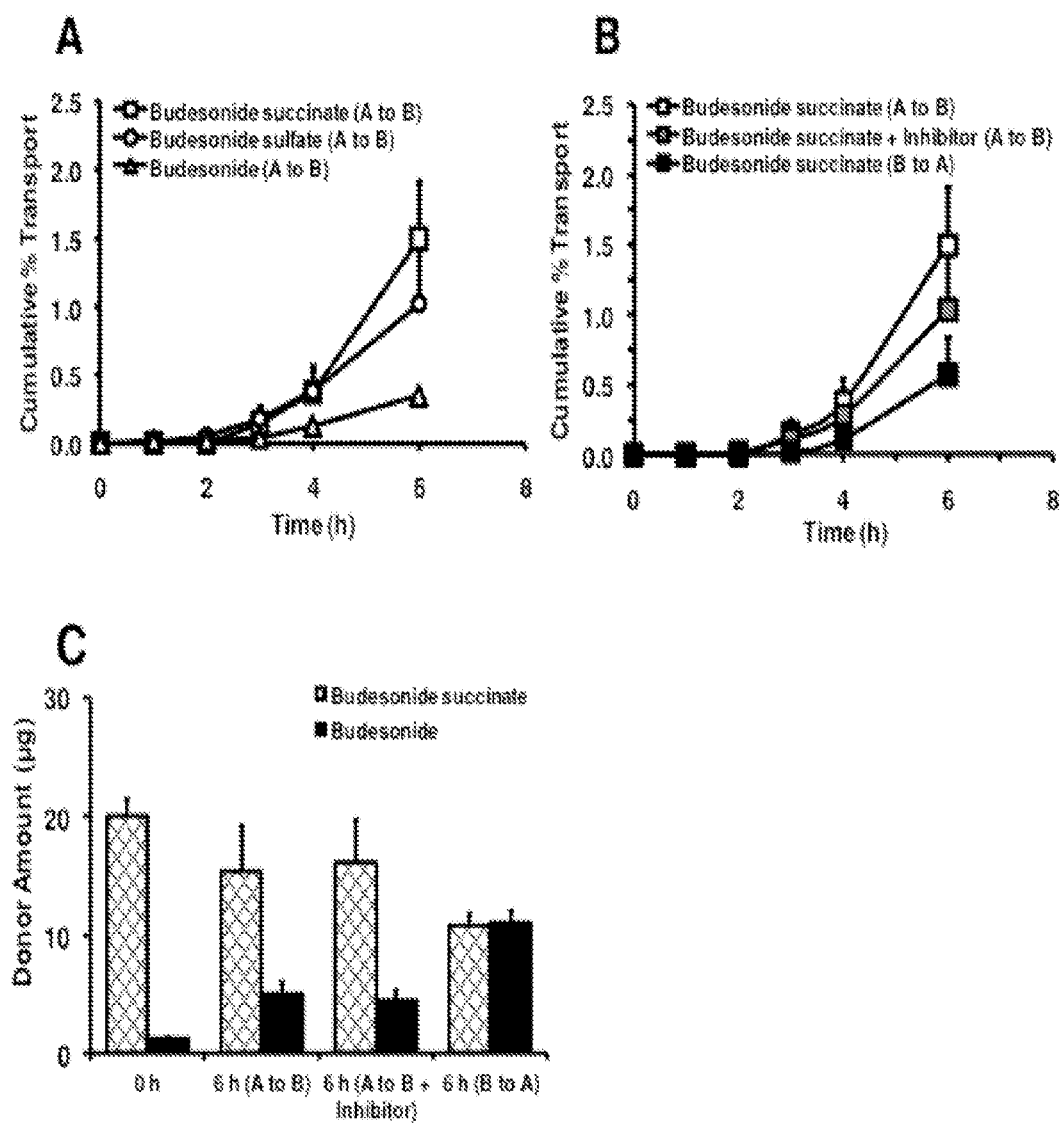
FIG. 2A is a graph showing transport of budesonide, budesonide sulfate and budesonide succinate across freshly excised bovine sclera-choroid-RPE (A to B means sclera towards RPE direction FIG. 2B is a graph showing transport of budesonide succinate across freshly excised bovine sclera-choroid-RPE in A to B and B to A direction (B to A means RPE towards sclera). Transport of this pro-drug was also conducted in presence of p-amino hippuric acid (a monocarboxylate transport inhibitor) in A to B direction.
FIG. 2C is a graph showing donor amounts of budesonide succinate and budesonide formed at time zero and at the end of the study (6 h) for transport studies shown in panel B. Data represents mean±sd (n=4).

In vitro transscleral transport of budesonide sulfate (1%) and budesonide succinate (1.5%) were not significantly different (FIG. 2). However, budesonide succinate transport was significantly ($p<0.05$) higher than budesonide (0.2%) across bovine sclera-choroid-RPE in sclera to RPE direction. Based on the higher cumulative percentage transport observed with budesonide succinate, we selected this pro-drug for our further investigations. Although a significant difference was not observed, transport of this pro-drug was reduced to 1% in presence of a monocarboxylic acid transporter inhibitor in sclera to RPE direction. Another important observation was that the transport of budesonide succinate was significantly higher (1.5%) in sclera to RPE direction compared to RPE to sclera direction (0.5%).

Figure 3:
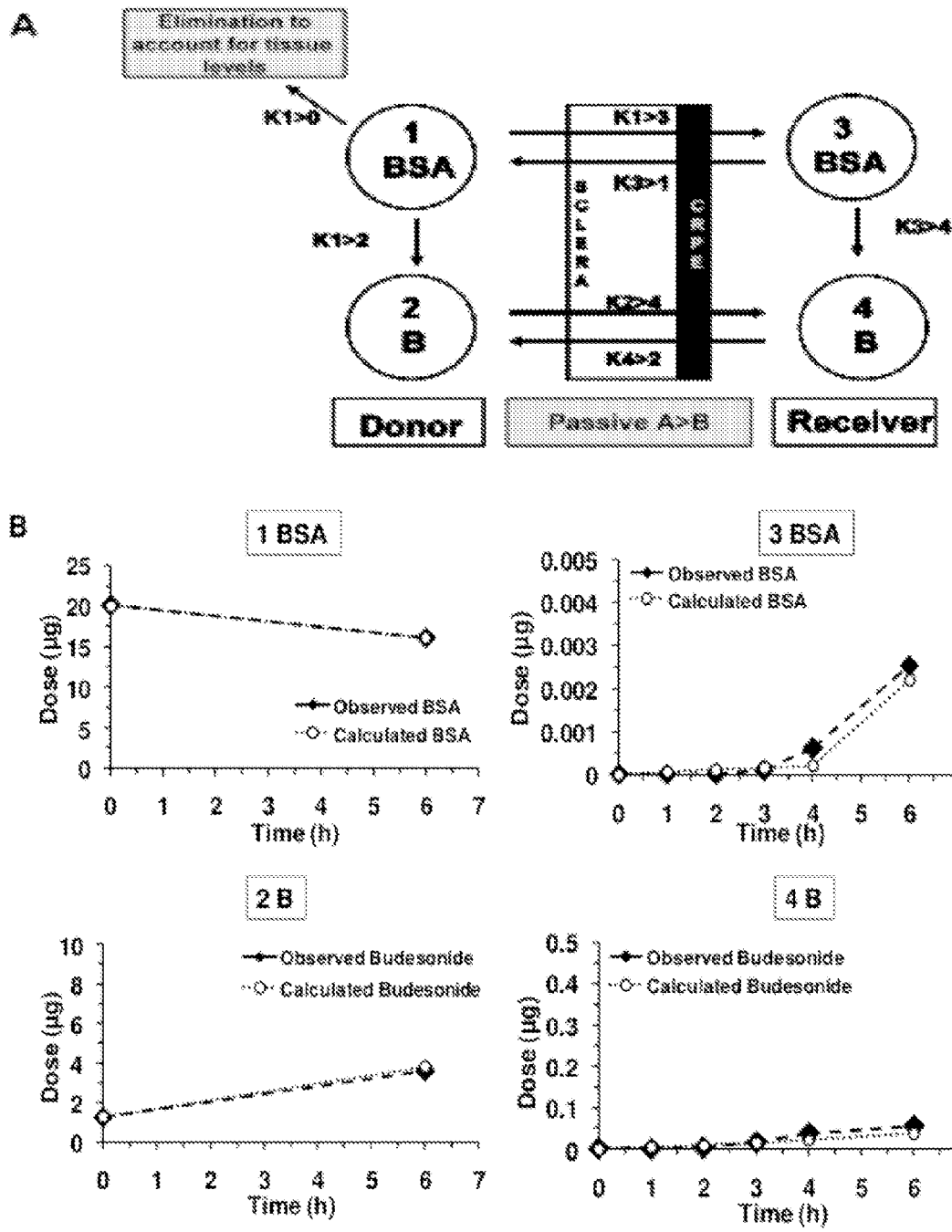
FIG. 3A is a schematic of a PK model for transport of budesonide succinate across bovine sclera-choroid-RPE in A to B direction. Circles on left side (1 BSA; 2 B) represent the donor chamber whereas circles on right side (3 BSA; 4 B) represent the receiver chamber for BSA transport in A to B direction. 2 B and 4 B were included and represent budesonide formed/transported during the course of transport study. A separate compartment was included to account for the pro-drug/parent drug loss due to tissue absorption. K1>0 represents rate constant for drug loss into the tissue, K1>2 and K3>4 represent rate constants for pro-drug conversion into parent drug on donor and receiver side respectively. K1>3 and K2>4 represent the transport rate constant for budesonide succinate and budesonide from donor to the receiver side. K3>1 and K4>2 represent transport rate constant for budesonide succinate and budesonide from receiver to the donor side (backward movement, if any).
FIG. 3B includes graphs showing the observed and model predicted amounts of pro-drug and parent drug in donor and receiver chambers during the course of transport study.
Figure 4:
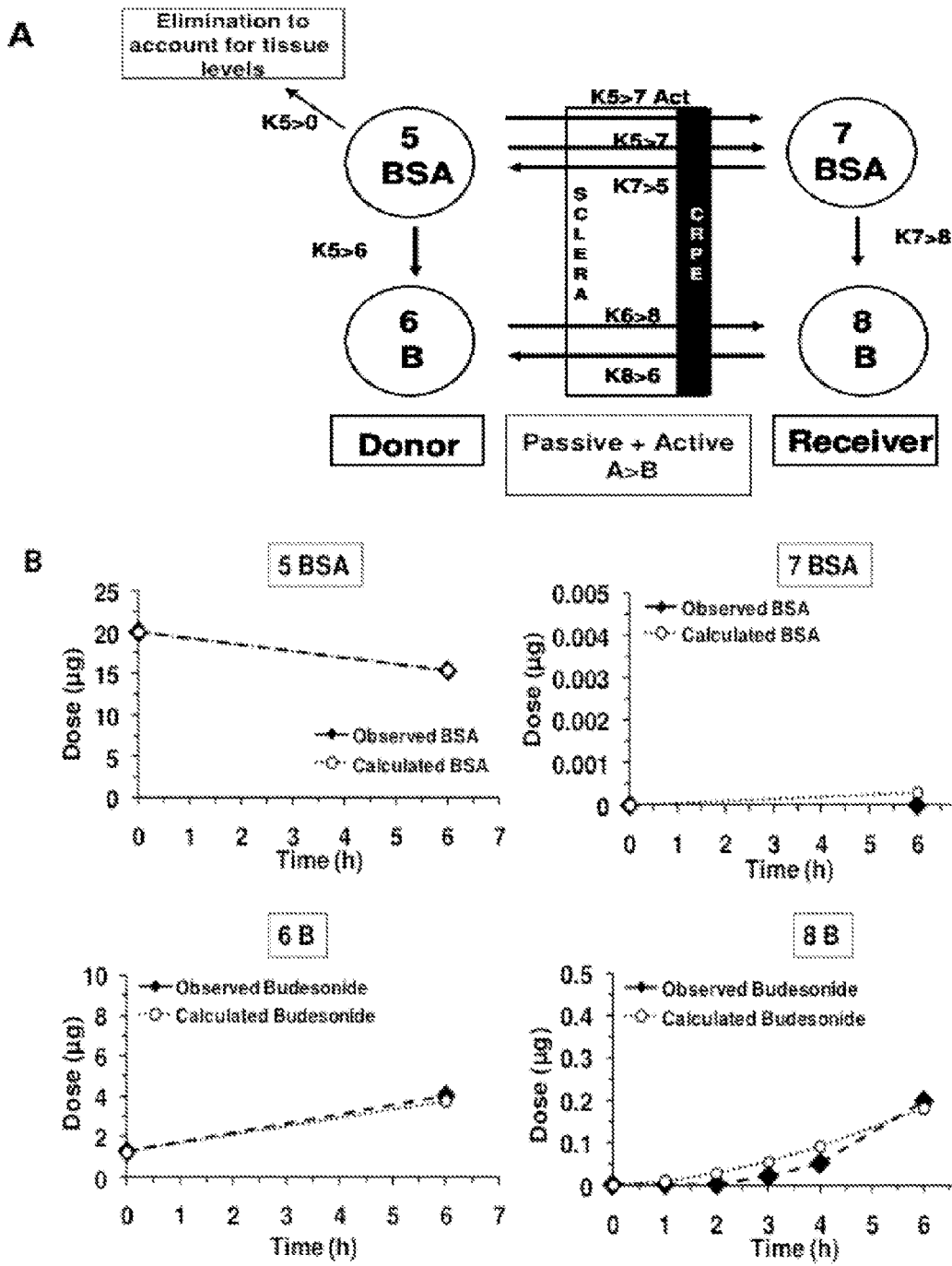
FIG. 4A is a schematic showing a PK model for transport of budesonide succinate across bovine sclera-choroid-RPE in A to B direction in presence of an inhibitor. Circles on left side (5 BSA; 6 B) represent the donor chamber whereas circles on right side (7 BSA; 8 B) represent the receiver chamber for BSA transport in A to B direction. 6 B and 8 B were included and represent budesonide formed/transported during the course of transport study. A separate compartment was included to account for the pro-drug/parent drug loss due to tissue absorption. K5>0 represents rate constant for drug loss into the tissue, K5>6 and K7>8 represent rate constants for pro-drug conversion into parent drug on donor and receiver side respectively. K5>7 and K6>8 represent the transport rate constant for budesonide succinate and budesonide from donor to the receiver side. K5>7 Act represent active transport rate constant and contribution (0.5%) of active diffusion in BSA transport. K7>5 and K8>6 represent transport rate constant for budesonide succinate and budesonide from receiver to the donor side (backward movement, if any).
FIG. 4B are graphs showing the observed and model predicted amounts of pro-drug and parent drug in donor and receiver chambers during the course of transport study.
Figure 5:
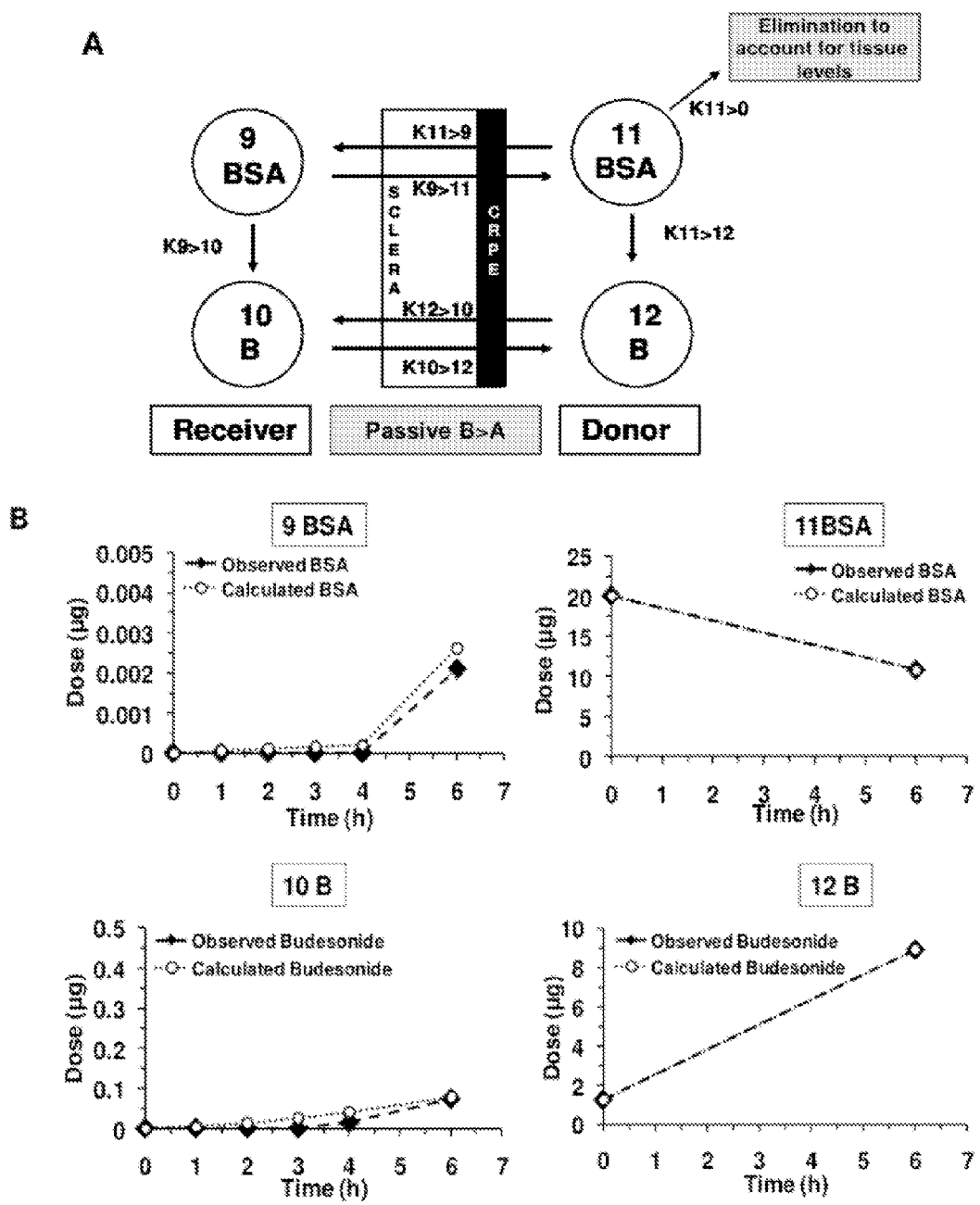
FIG. 5A is a schematic showing a PK model for transport of budesonide succinate across bovine sclera-choroid-RPE in B to A direction. Circles on left side (9 BSA; 10 B) represent the receiver chamber whereas circles on right side (11 BSA; 12 B) represent the donor chamber for BSA transport in B to A direction. 12 B and 10 B were included and represent budesonide formed/transported during the course of transport study. A separate compartment was included to account for the pro-drug/parent drug loss due to tissue absorption. K11>0 represents rate constant for drug loss into the tissue, K11>12 and K9>10 represent rate constants for pro-drug conversion into parent drug on donor and receiver side respectively. K11>9 and K12>10 represent the transport rate constant for budesonide succinate and budesonide from donor to the receiver side. K9>11 and K10>12 represent transport rate constant for budesonide succinate and budesonide from receiver to the donor side (backward movement, if any).
FIG. 5B are graphs showing the observed and model predicted amounts of pro-drug and parent drug in donor and receiver chambers during the course of transport study.

FIGS. 3, 4 and 5 compare the model predicted and observed dose amounts of budesonide succinate and budesonide in donor and receiver chambers during the course of study. Results have been presented in 3 separate figures from a simultaneous model run which included the observed dose amounts of pro-drug as well as parent drug from the transport studies in A to B, A to B+inhibitor and B to A direction. The best fit model after 20 runs had AIC value, $R^2$ and % CV of −33.65, 0.999 and ≤25% respectively.

Example 1.2

Method

All animals were handled according to the ARVO statement for the use of Animals in Ophthalmic and Vision Research. A suspension of budesonide and budesonide succinate (BSA, single prodrug of budesonide) was used for the ex vivo studies. one mg/ml suspension was made in sterilized phosphate buffer saline (pH 7.4) in presence of carboxymethyl cellulose sodium salt (low viscosity, 50-200 cP; Sigma-Aldrich, Cat# C5678) at a concentration of 0.5% w/v as a suspending agent. Drug suspensions were shaken before each posterior subconjunctival injection. Rats were divided into two groups. Group 1—Budesonide: animals were euthanized with 350 μl intraperitoneal injection of sodium pentobarbital (250 mg/Kg). Twenty-five microliters of budesonide suspension was injected using a 30 G needle in the posterior subconjunctival space of one eye of each animal and the other eye was not treated. At the end of 1 h, eyes were enucleated and immediately frozen in dry ice and isopentane bath. All samples were stored at −80° C. until LCMS/MS analysis. Group 2—Budesonide succinate (BSA): animals were euthanized as mentioned above. Immediately after euthanasia, animals were administered with 25 μl suspension of budesonide succinate (1 mg/ml) in one eye via posterior subconjunctival injection using a 30 G needle and the other eye was left untreated. At the end of 1 h, the eyes were enucleated and frozen in a similar manner as above until analysis. Periocular tissue samples were also collected from both the groups at the end of the study. Different ocular tissues including sclera, choroid-RPE, retina, and vitreous were isolated and analyzed for drug levels.

Results

Figure 6:
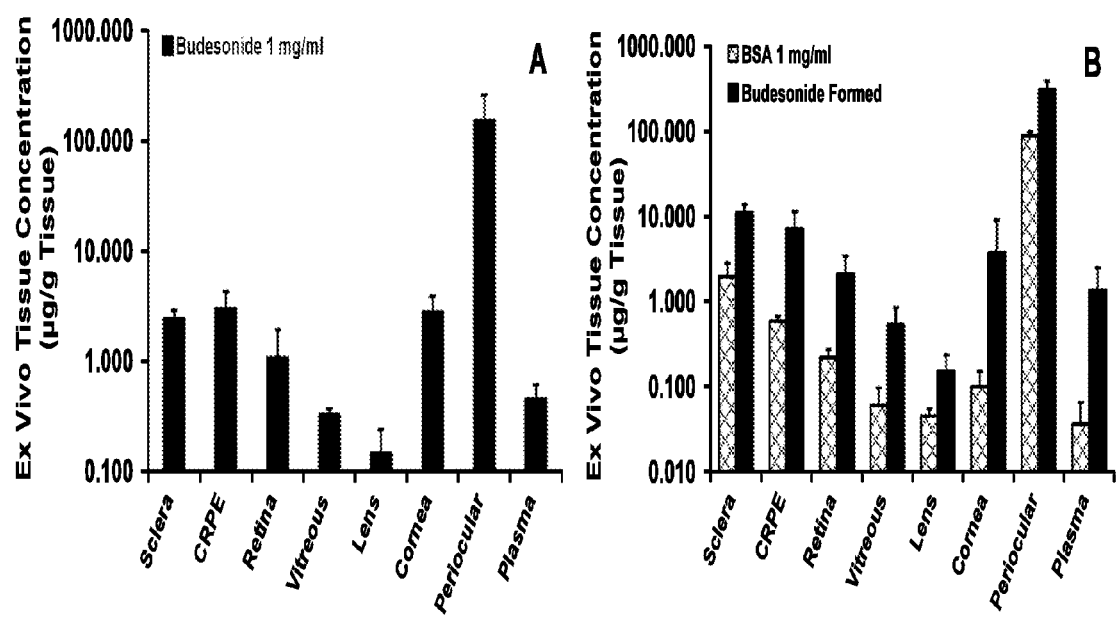
FIG. 6 are graphs showing the ex vivo transscleral delivery of A) budesonide and B) budesonide succinate at the end of one hour in Brown Norway (BN) rats. Twenty five microliters of 1 mg/ml suspension was injected into the posterior subconjunctival space of euthanized (ex vivo study) rats. Panel B represents ocular tissue leves of BSA and budesonide formed from BSA. Data is expressed as mean±SD for n≥3.
Figure 7:
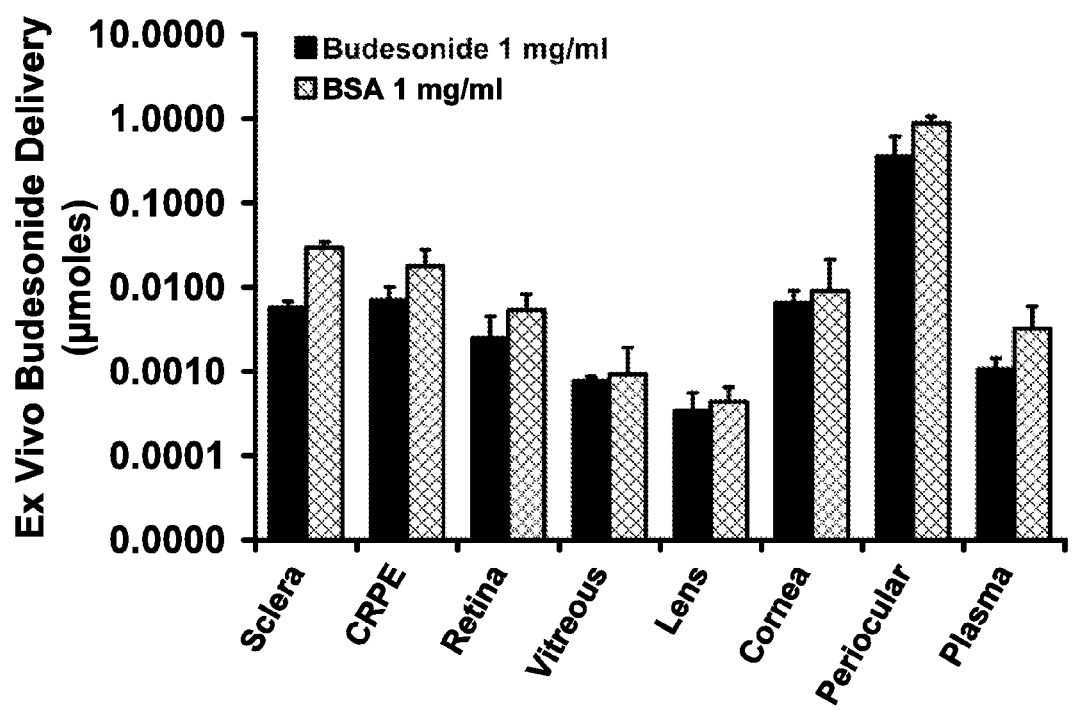
FIG. 7 is a graph showing a comparison of ex vivo budesonide delivery in different ocular tissues following posterior subconjunctival injection of twenty five microliters of 1 mg/ml suspension of budesonide and budesonide succinate at the end of one hour in Brown Norway rates. Data is expressed as mean±SD for n≥3.

The ex vivo drug levels in sclera, CRPE, retina, and vitreous for the budesonide (Group 1) were 2.4, 3.0, 1.0, and 0.3 μg/g tissue. The ex vivo drug levels in sclera, CRPE, retina, and vitreous for the budesonide succinate (Group 2) were 1.9, 0.6, 0.2, and 0.05 μg/g tissue. The ex vivo drug levels in the above tissues for budesonide released from budesonide succinate (Group 2) were 11.0, 7.2, 2.2, and 0.5 μg/g tissue. Overall, the budesonide delivery in sclera, choroid-RPE and retina was 2-5 folds higher with the prodrug, budesonide succinate (Group 2) as compared to the plain drug budesonide (Group 1). Results are shown in FIGS. 6 and 7

Example 2

Materials and Methods

Celecoxib was purchased from Spectrum chemical and laboratory products (New Brunswick, N.J., USA). Celecoxib succinamidic acid (C-SA, single pro-drug of celecoxib) and celecoxib succinamidic acid taurine (C-SA-T, double pro-drug of celecoxib) were synthesized in the laboratory. Succinic anhydride, dimethylamino pyridine, triethylamine, carbonyl diimidazole, N,N dimethyl formamide (anhydrous), tetrahydrofuran (anhydrous), taurine, natural melanin (isolated from Sepia officinalis), triton-X and EDTA were purchased from Sigma Aldrich (St. Louis. Mo., USA). All reagent grade organic solvents such as chloroform, dichloromethane, ethyl acetate, methanol and acetone were purchased from ACROS ORGANICS (New Jersey, USA). PBS pH 7.4 was used as a vehicle for all titrations and in vitro/in vivo studies. Freshly excised bovine eyes were purchased from G & C meat company, Colorado Springs. Male Brown-Norway (BN; pigmented) rats weighing 150 to 200 g were purchased from Charles River Laboratories, Wilmington, Del., USA.

Synthesis of Celecoxib-Sussinamidic Acid Pro-Drug (C-SA)

Celecoxib (2.62 mmoles) was dissolved in anhydrous THF under argon atmosphere. DMAP and TEA (3.15 mmoles each) were added while stirring. After 5-10 minutes, succinic anhydride (3.15 mmole) was added and reaction mixture was stirred overnight (16-18 h) at room temperature after which it was refluxed for 5-6 h (FIG. 8). At the end of 24 h, when there was no further increase in the intensity of the TLC spot for the product and the reaction was stopped. The organic layer was collected and concentrated to a viscous material on rotary evaporator. The viscous material was dissolved in minimum volume of dichloromethane and washed once with equal volume of water. Final product in the organic layer was purified by column chromatography. Silica gel 60 (Geduran, particle size 40-63 µm, EMD Chemicals) and dichloromethane/methanol were used as stationary phase and mobile phase respectively.

Synthesis of Celecoxib-Succinamidic Acid-Taurine Prodrug (C-SA-T)

This is a two-step process starting from C-SA prodrug as shown in FIG. 8. Terminal carboxylic acid functionality in celecoxib-succinamidic acid (1 mmole) was first activated with carbonyl diimidazole (CDI) and then reacted with taurine in presence of triethylamine as catalyst. One mmole of C-SA was dissolved in anhydrous dimethyl formamide (DMF) and CDI (1.5 mmoles) dissolved in anhydrous DMF was added dropwise at 0° C. over a period of 1 h. The reaction mixture was stirred for another 1 h at 0° C. Taurine (2 mmoles) suspended in minimum volume of water along with triethylamine (2 mmoles) was added dropwise to the above reaction mixture and stirred at room temperature for 24 h. The reaction mixture was concentrated under high vacuum. The solid mixture was dissolved in dichloromethane-acetonitrile-water (90:5:5) and purified product was obtained after column chromatography as done previously for CSA.

In Vitro Transport Across Bovine Cornea, Conjunctiva and Sclera-Choroid-RPE

Freshly excised bovine eyes procured from a local slaughter house were used for all in vitro transport studies. Fatty or adherent tissue all around the eye is removed first. Cornea and conjunctiva were then removed. For isolation of sclera and choroid-RPE (CRPE), the anterior segment of the eye was removed with a circumferential cut below the limbus. The eye was cut into two halves along the geometric axis, a line joining the anterior pole (corneal center) and the posterior pole (center of the scleral curve), and the vitreous was removed. Neural retina was removed by exposing the eyecup to isotonic assay buffer at pH 7.4. Equatorial region of the remaining sclera-choroid-RPE (SCRPE) was used as is for SCRPE transport studies. All transport studies for celecoxib were performed in presence of 5% HP-β-CD. Transport of C-SA-T was also performed in B to A direction across SCRPE. Drug solutions were prepared in the following manner: Celecoxib (100 µg/ml) in presence of 5% HP-β-CD was made after triturating celecoxib with HP-β-CD in a pestle-mortar followed by addition of assay buffer. The mixture was stirred for 24 h. Before use, the clear solution was filtered through 0.2µ filter. C-SA and C-SA-T (100 µg/ml) pro-drug solutions were made just before the start of the experiment followed by filtration through 0.2µ filter. All transport experiments were performed for 6 h at 37° C. Samples were collected at regular time intervals from the receiver side with replacement with fresh assay buffer (pH 7.4). Transport studies with all solutes were performed in A to B direction meaning outward to inward (eg. sclera towards choroid-RPE) movement of the solute was measured. Transport for C-SA-T was also performed in B to A direction meaning inward to outward movement (choroid-RPE towards sclera) for this solute was also measured. Samples from all the transport studies were analyzed on LC-MS/MS.

Isothermal Titration Calorimetry for Melanin Binding Estimation

Following parameters were used for calculating the melanin binding of celecoxib/C-SA in the ITC titration: melanin=1 mg/ml suspension in PBS (pH 7.4), celecoxib=2 µg/ml in PBS (pH 7.4) and CSA=250 µg/ml in PBS (pH 7.4), 60 injections of 5 µl each, injection duration=10.3 sec, spacing between two consecutive injections=300 sec, stirring speed=595 rpm, temperature=37° C. All samples were degassed before ITC injections. For calculating the heat of dilution, celecoxib/C-SA was titrated against PBS using the same injection parameters.

In Vivo Delivery Assessment of Celecoxib/C-SA/C-SA-T Eye Drops in Male Brown Norway (BN) Rats Two mg/ml suspension of celecoxib, 2 mg/ml solution of C-SA and C-SA-T, 10 mg/ml solution of C-SA-T was made in PBS pH 7.4. 10 µl eye drop of celecoxib (n=6 eyes; 3 animals), C-SA and C-SA-T (n=8 eyes; 4 animals) was administered to both the eyes of each BN rat. At the end of 1 h, the animals were euthanized and the eyes were enucleated. Periocular tissue and plasma samples were collected.

Sample processing: Acetonitrile precipitation method was used for drug extraction from the tissues. Briefly, eyes from each eye drop study were dissected for tissue isolation. Tissues were homogenized in 250 µl water (pH 7.4 adjusted with 5 mM ammonium acetate) containing indoprofen as internal standard at a concentration of 500 ng/ml (1000 ng/ml stock was made). Similar volume of acetonitrile was added and mixed well by vortexing for 30 minutes. Samples were centrifuged at 15,000 rpm for 30 minutes. Supernatant was collected for LC-MS/MS analysis.

LC-MS/MS Method

Mass Parameters: The mass spectrometric parameters of celecoxib, C-SA, C-SA-T and indoprofen (internal standard) were optimized in negative ionization mode by infusing a 1.0-µg/mL solution on a liquid chromatography tandem mass spectrometry instrument (API 3000; PE SCIEX, Concord, Ontario, Canada) by the syringe infusion mode. All analytes were monitored in multiple reaction monitoring (MRM) mode (celecoxib 380/316, C-SA 480/380, C-SA-T 587/206 and indoprofen 280/236). LC parameters: Zorbax SB C18 (3.5 µm, 2.1×100 mm) column; 5 mM ammonium formate (pH 6.8, mobile phase A) and acetonitrile (mobile phase B) as mobile phase in gradient elution mode; flow rate 0.4 ml/min, column temperature 25° Celsius. Total run time was 5.5 min.

Efficacy Assessment of C-SA and C-SA-T Eye Drops in Streptozotocin-Induced Diabetic Retinopathy Rat Model Diabetes Induction: BN rats weighing 175-225 g were acclimatized for at least two days before any experimental procedure. After overnight fasting for 12-16 h, an intraperitoneal injection of 30 mg/ml solution of streptozotocin in 10 mM citrate buffer (pH 4.5) was administered (60 mg/kg body weight) to induce diabetes. After 3-4 h of streptozotocin injection, animals were put on regular diet and 24 h after streptozotocin injection, blood sample (5-10 µl) was collected via tail vein. The blood glucose levels in the animals were determined with a glucose monitor (One Touch; Life Scan Inc., Milpitas, Calif.). Animals with blood glucose levels greater than 250 mg/dL were considered diabetic. The animals were divided into four groups. Group 1: Normal (N=12), Group 2: Diabetic+vehicle (N=12), Group 3: Diabetic+0.2% w/v C-SA eye drops (N=12) and Group 4: Diabetic+1.0% w/v C-SA-T eye drops (N=12). Treatment was started immediately after diabetes induction. Both eyes were dosed twice daily for 60 days in group 2, 3 and 4 with their respective treatment. Animals in groups 2-4 were sacrificed at the end of 2 months. Normal animals in group 1 were sacrificed immediately after acclimatization in the animal facility. For each of the three assays, namely, FITC-Dextran leakage, vitreous-to-plasma protein ratio, and leukostasis, we used 4 animals from each of the four groups mentioned above.

Blood Retinal Barrier Leakage

Retinal FITC-Dextran Leakage: BN rats from each group were used for the assessment of FITC-dextran leakage. At 1 hpur after last dosing on day 61, rats were sacrificed for FITC-dextran leakage assay. Brief protocol for the assay and tissue sample processing is described below. First, the animals were anesthetized with ketamine (80 mg/kg) and xylazine (12 mg/kg) administered intraperitoneally. Then a 50 mg/ml PBS (pH 7.4) solution of FITC-dextran with a molecular weight of 4.4 kDa was administered (50 mg/kg body weight) intravenously via tail vein. Animals were euthanized with 150 mg/kg sodium pentobarbital after 10 minutes (circulation time for FITC-dextran) of tail vein injection. Blood samples (0.5-1 ml) were withdrawn from the heart in 2 ml Eppendorf tubes (SureLock Microcentrifuge Tubes, LIGHTLABS, USA) containing 50 µl of EDTA. Chest cavity was opened. Animals were perfused with PBS (500 ml/kg body weight) for 6-7 minutes after a 20 G needle attached to a 50 ml syringe was inserted into the left ventricle. Eyes were enucleated and isopentane-dry ice bath was used to immediately snap-freeze the eyes before storing them at −80° C. Retina of each eye was isolated, weighed and homogenized in 500 µl of PBS (pH 7.4). Following homogenization, 500 µl of PBS containing 2% Triton X-100 was added to the homogenate. The mixture was vortexed at room temperature for 1 h. The homogenate was centrifuged at 15000 rpm (21,130 g) for 20 min and the supernatant was collected. The relative FITC-dextran fluorescence units in 1 ml of supernatant were measured using a spectrofluorometer set at an excitation wavelength of 483 nm and an emission wavelength of 538 nm. Fluorescence of blank PBS was also measured for subtraction from each sample reading. Final concentration of FITC-dextran was expressed as µg/g tissue. Standard curve was generated using known amounts of FITC-dextran (5 ng/ml to 5 µg/ml). 20 µl (~20 mg) of plasma was diluted to 1 ml (50 times dilution) with PBS for quantification under the linear range of the standard samples. The dilution factor was taken into account for estimating the amount of FITC-dextran per microliter of blood sample. The amount of FITC-dextran leakage in to the ocular tissues was calculated using the following equation, after correcting for dilutions.

$$\frac{\frac{Retinal\ FITC-dextran(\mu g)}{retinal\ weight\ (g)}}{Plasma\ FITC-dextran\ (\mu g/\mu l) \times circulation\ time\ (min)}$$

Vitreous-to-Plasma Protein Ratio: BN rats from each group were used for the assessment of vitreous to plasma protein ratio. At 1 h after last dosing on day 61, rats were sacrificed for determining the protein ratio. Rats were euthanized with 150 mg/kg sodium pentobarbital administered intraperitoneally. Eyes were enucleated and isopentane-dry ice bath was used to immediately snap-freeze the eyes before storing them at −80° C. Blood samples (0.5-1 ml) were withdrawn from the heart following cardiac puncture in 2 ml Eppendorf tubes (SureLock Microcentrifuge Tubes, LIGHTLABS, USA) containing 50 µl of EDTA. The above samples were centrifuged at 15,000 g at 4° C. for 15 min to collect the plasma in the supernatant. Plasma samples were stored at −80° C. Ocular tissues including the retina and the vitreous from each eye were isolated and weighed. The vitreous was allowed to liquefy. The vitreous samples were centrifuged at 15,000 g at 4° C. for 20 min. The supernatant of vitreous was collected (20 µl) in new Eppendorf tubes and weighed (weight range=19-21 mg). The supernatant (20 µl) was diluted to 1 ml with PBS (pH 7.4) (50 times dilution). One hundred microliters of the above diluted material was mixed with 1 ml of Bradford reagent. Absorbance of the above 1 ml volume was measured at 595 nm. The plasma sample (20 µl) was also diluted to 1 ml with PBS (pH 7.4) (50 times dilution). One hundred µl of the above diluted material was mixed with 1 ml of Bradford reagent. Absorbance of the above 1 ml volume was measured at 595 nm. The standard curve was generated using known concentrations of bovine serum albumin (25-500 µg/ml in PBS, pH 7.4). Hundred microliters of each standard was mixed with 1 ml of Bradford reagent. The amount of protein in plasma and vitreous was estimated from the standard curve after correcting for dilutions.

Retinal Leukostasis

BN rats from each group were used for the assessment of adherent leukocytes. At 1 hour after last dose on day 61, rats were sacrificed for ex-vivo retinal leukostasis assay. First, the animals were anesthetized with ketamine (80 mg/kg) and xylazine (12 mg/kg) administered intraperitoneally. Then, the chest cavity was carefully opened and animals were perfused with PBS (250 ml/kg body weight) for 6-7 minutes after inserting a 20 G needle attached to 50 ml syringe into the left ventricle. Animals were then perfused with a 40 µg/ml PBS (pH 7.4) solution of FITC-conjugated concanavalin A lectin (5 mg/kg, ~33 ml) to label the adherent leukocytes and the vascular endothelial cells. Animals were perfused again with similar volume of PBS as above to remove unbound lectin. Eyes were enucleated and fixed in 2% paraformaldehyde for 2 h. Retinas were carefully removed to prepare the flat mounts. Fluorescence microscope (Digital Eclipse C1; Nikon Inc., Melville, N.Y.) under blue light (Ex 465-495, DM 505, BA 515-555) with a 20× objective was used to count the number of leukocytes adhered to the vessel walls. The count was compared between treated and untreated rats.

Statistical Analyses

All data in this study are expressed as the mean±S.D. Comparisons between two groups were done by Student's t-test whereas comparisons among multiple groups were done using one-way ANOVA followed by a Tukey post hoc analysis. Statistical significance was set at $p \leq 0.05$ Results Synthesis and Characterization of Celecoxib-Succinamidi Acid (C-SA) and Celecoxib-Succinamidic Acid-Taurine (C-SA-T) Pro-Drugs.

The overall yield of C-SA (single amide prodrug of celecoxib) was 75-80%. Structure of C-SA was confirmed from the spectral data of $^1$HNMR and MS (TOF, ES). $^1$HNMR (CDCl$_3$) δ 2.3 (s, 3H), 2.5 (t, 2H), 2.7 (t, 2H), 6.8 (s, 1H), 7.0 (d, 2H), 7.2 (d, 2H), 7.4 (d, 2H), 7.8 (d, 2H), 9.9 (s, 1H). MS (TOF, ES) (m/z) 479.97, 379.99. The overall yield of C-SA-T (double amide prodrug of celecoxib) was 55-60%. Structure of C-SA-T was confirmed from the spectral data of $^1$HNMR and MS (TOF, ES). $^1$HNMR (CDCl$_3$) δ 2.3 (s, 3H), 2.5 (t, 2H), 2.7 (t, 2H), 3.6 (t, 2H), 3.7 (t, 2H), 6.8 (s, 1H), 7.0 (d, 2H), 7.2 (d, 2H), 7.4 (d, 2H), 7.8 (d, 2H), 9.9 (s, 2H) MS (TOF, ES) (m/z) 587.04, 480.01, 380.04.

In Vitro Transport Across Bovine Cornea, Conjunctiva and Sclera-Choroid RPE

Figure 9:
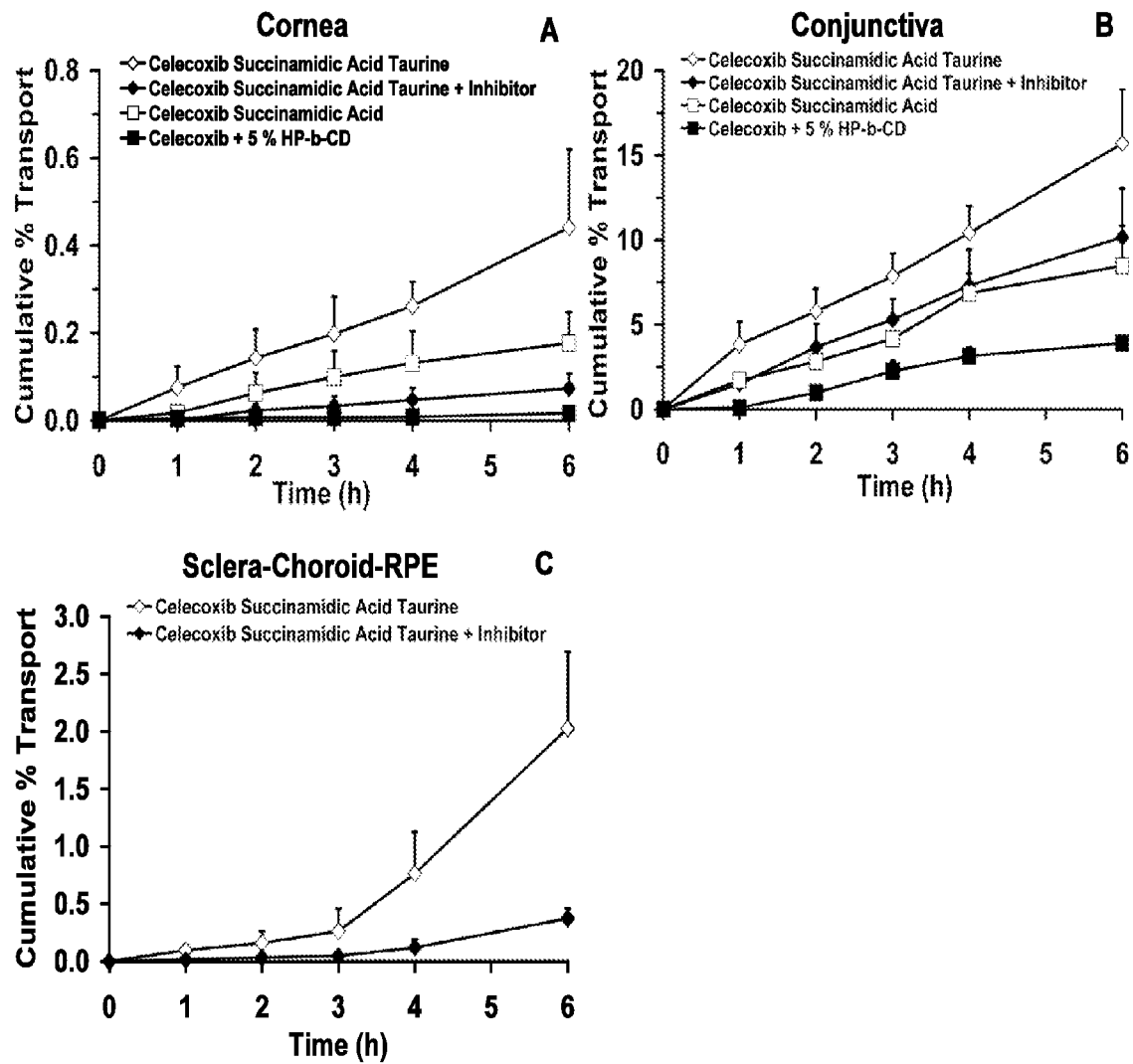
FIG. 9A-C are graphs showing cumulative percentage transport (N≥4) of celecoxib succinamidic acid taurine (C-SA-T) double prodrug was higher than C-SA and celecoxib across A) cornea, B) conjunctiva as well as C) sclera-choroid-RPE. Transport of double pro-drug was significantly reduced in the presence of an inhibitor (Taurine) across cornea and sclera-choroid-RPE. Data represents mean±s.d.

Cumulative percent transport (FIG. 9) of celecoxib (5% HP-β-CD), C-SA and C-SA-T at the end of 6 h across bovine cornea was 0.017, 0.177 and 0.441% respectively. Transport of C-SA and C-SA-T was found to be approximately 10- and 25-times higher than celecoxib. Transport of celecoxib (5% HP-β-CD), C-SA and C-SA-T across bovine conjunctiva was 3.9, 8.4 and 15.6% respectively. Transport of C-SA and C-SA-T was found to be approximately 2- and 4-times higher than celecoxib. Transport of celecoxib (5% HP-β-CD), C-SA and C-SA-T across bovine sclera-choroid-RPE was approximately 0.1, 1.0, and 2.0% respectively. Transport of C-SA and C-SA-T was found to be approximately 10- and 20-times higher than celecoxib. The effect of taurine as an inhibitor was seen with a >50% reduction in the transport of C-SA-T across cornea and SCRPE.

Melanin Binding Estimation Using Isothermal Titration Calorimetry

Figure 10:
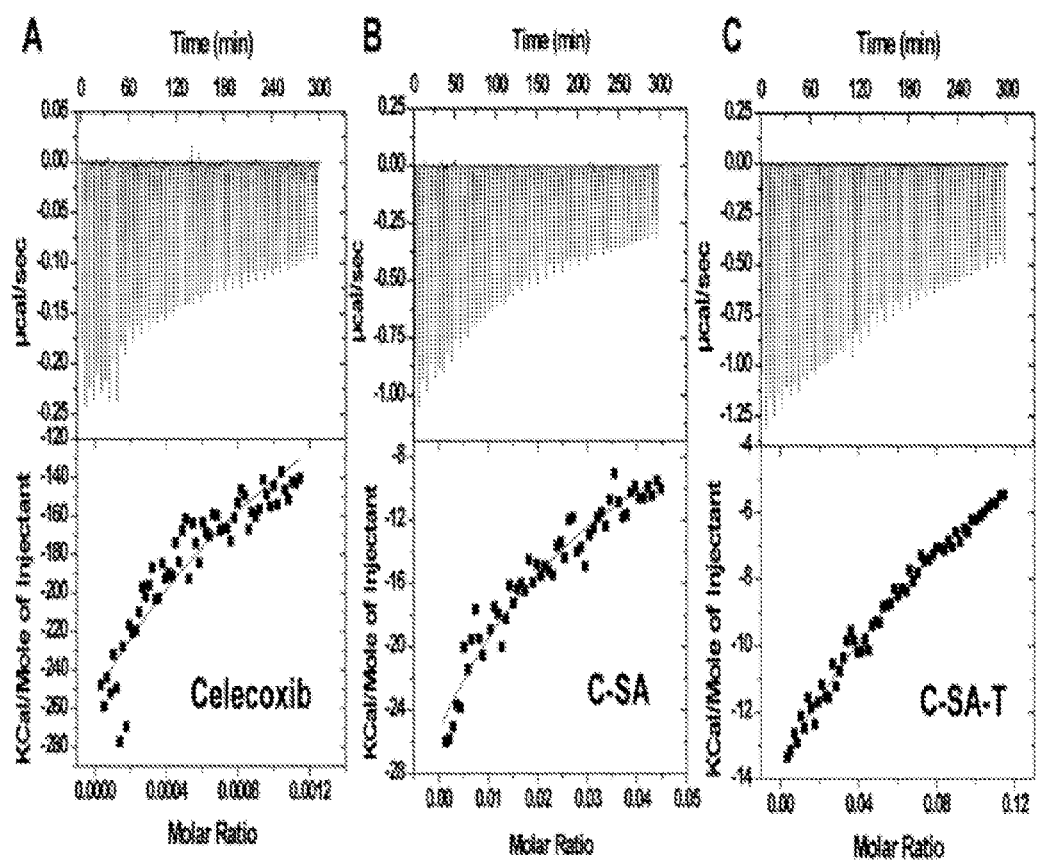
FIG. 10A-C are graphs showing isothermal titration calorimetry (ITC) thermograms representing the binding of A) celecoxib (2 μg/ml); B) C-SA (single pro-drug, 250 μg/ml); and C) C-SA-T (double pro-drug, 250 μg/ml) with 1 mg/ml suspension of melanin in PBS (pH 7.4). Melanin binding of C-SA-T (K=7.93 E3 $M^{-1}$) and C-SA (K=8.89 E3 $M^{-1}$) was ~130-110 fold lower than that of celecoxib (K=1.01 E6 $M^{-1}$).
Figure 11:
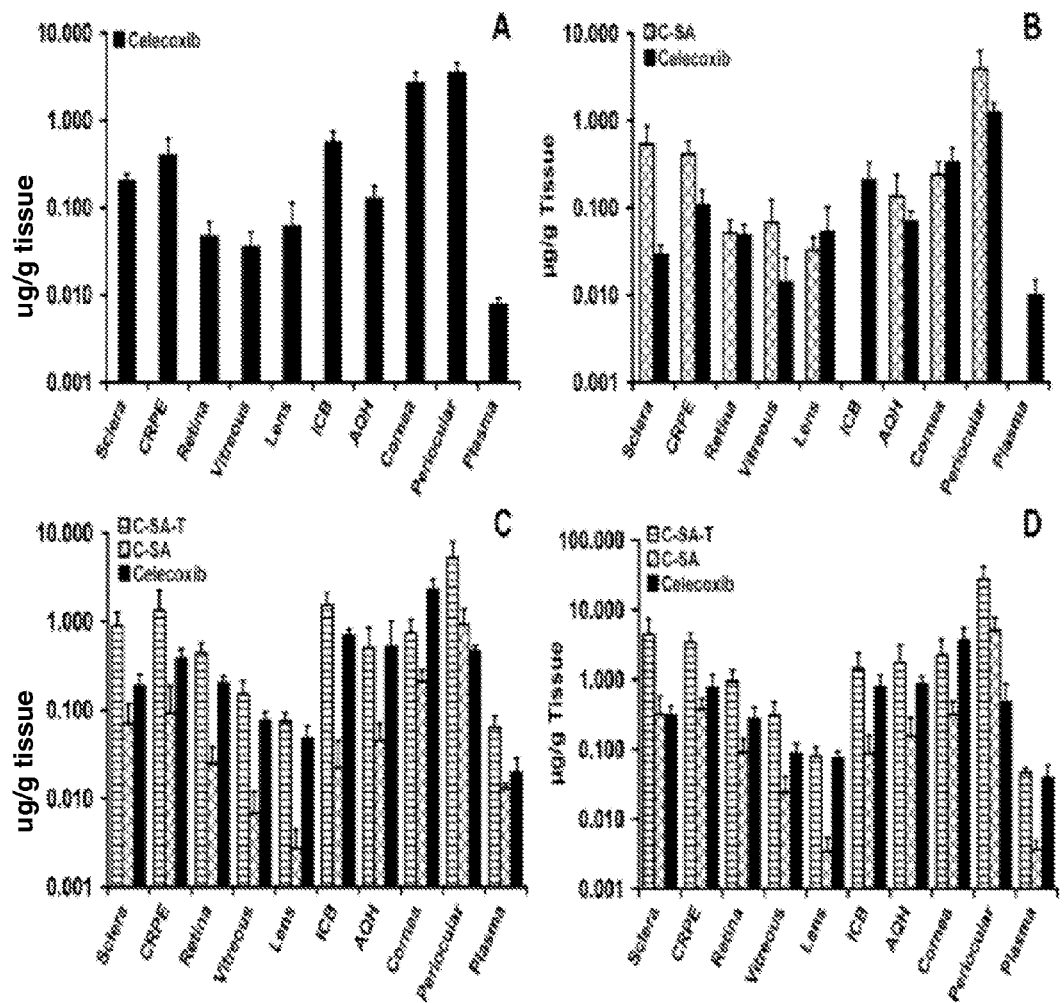
FIG. 11A-D are graphs showing ocular biodistribution at the end of 1 h after administration of 10 μl drop of A) celecoxib (2 mg/ml), B) C-SA (2 mg/ml), C) C-SA-T (2 mg/ml), and D) C-SA-T (10 mg/ml) in BN rats. Data represents mean±sd (n=6-8 eyes, 3-4 animals). Panels B, C, D represent the levels of pro-drug as well as parent drug formed.
Figure 12:
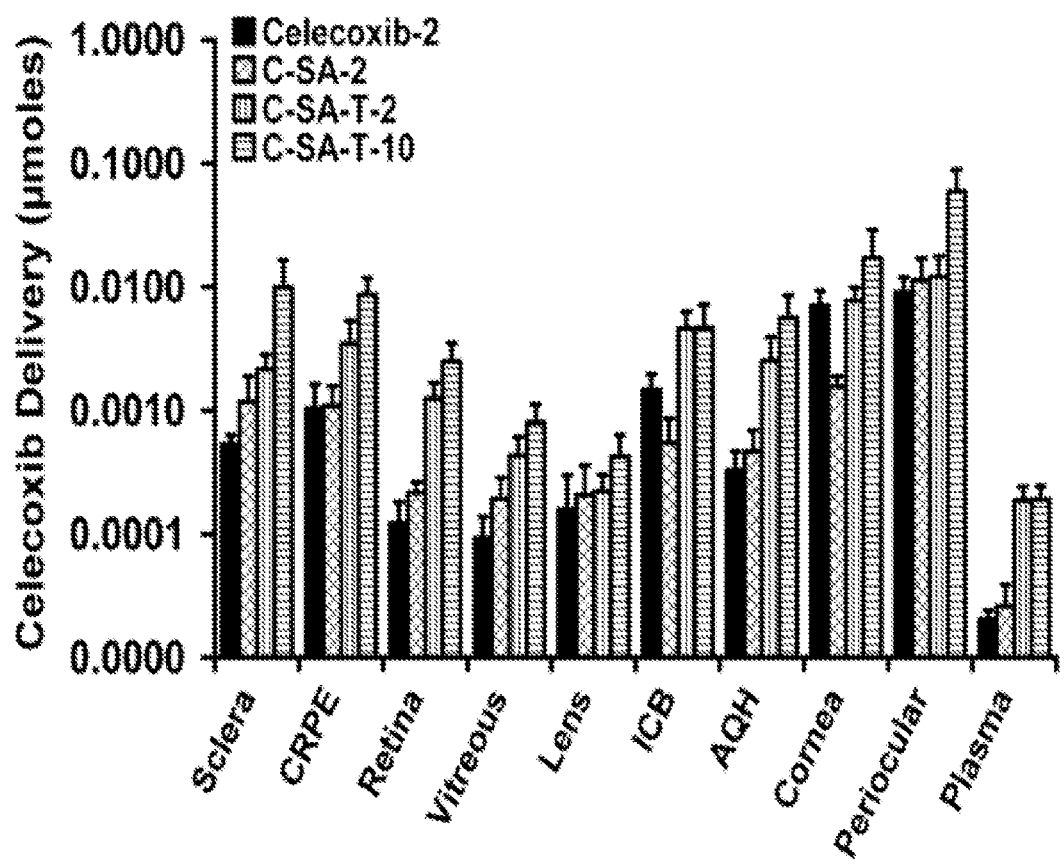
FIG. 12 is a graph showing ocular biodistribution of celecoxib at the end of 1 h after administration of 10 μl drop of celecoxib (2 mg/ml), C-SA (2 mg/ml), C-SA-T (2 mg/ml), and C-SA-T (10 mg/ml) in BN rats. Data represents mean±sd (n=6-8 eyes, 3-4 animals).

FIG. 10A-C represents the melanin binding of celecoxib, C-SA and C-SA-T with natural melanin. The value of binding/association constant for celecoxib with melanin was found to be Ka=$1.01 \times 10^6$ M$^{-1}$. Whereas, similar value for C-SA and C-SA-T binding with melanin was found to be $8.89 \times 10^3$ M$^{-1}$ and $7.39 \times 10^3$ M$^{-1}$ respectively, which was approximately 110 to 130 fold lower than melanin binding affinity of celecoxib. Furthermore, we used C-SA at a concentration 125 times higher than celecoxib for our binding experiments. In generating the pro-drug, a slightly basic and positively charged sulphonamide group of celecoxib was converted into acidic/negatively charged succinamidic acid. It is generally believed that acidic/negatively charged groups bind less with melanin as compared to basic/positively charged groups.

In Vivo Delivery of Celcoxib/CSA as Eye Drops in Brown Norwary Rats

Levels of celecoxib in cornea was higher than CSA which may be attributed to the highly lipophilic nature of celecoxib. Another important factor may be the viscosity of celecoxib suspension which was observed to be much higher than that of CSA. Similarly, levels of celecoxib were higher in iris and CRPE than C-SA possibly because of the highly pigmented nature of these tissues. However, levels of celecoxib in periocular space were observed to be lower than that of CSA. In all other tissues except for cornea, iris and CRPE, levels of CSA were higher than that of celecoxib. Retinal delivery was almost double with C-SA when compared to celecoxib. Levels of celecoxib with C-SA-T prodrug were higher in all tissues when compared with the parent drug. Enhancement in retinal delivery with 0.2% w/v and 1% w/v C-SA-T after topical administration was found to be about 10 and 20 folds respectively compared to celecoxib.

Efficacy Assessment of C-SA and C-SA-T Eye Drops in Streptozotocin-Induced Diabetic Retinopathy Rat Model.

Figure 13:
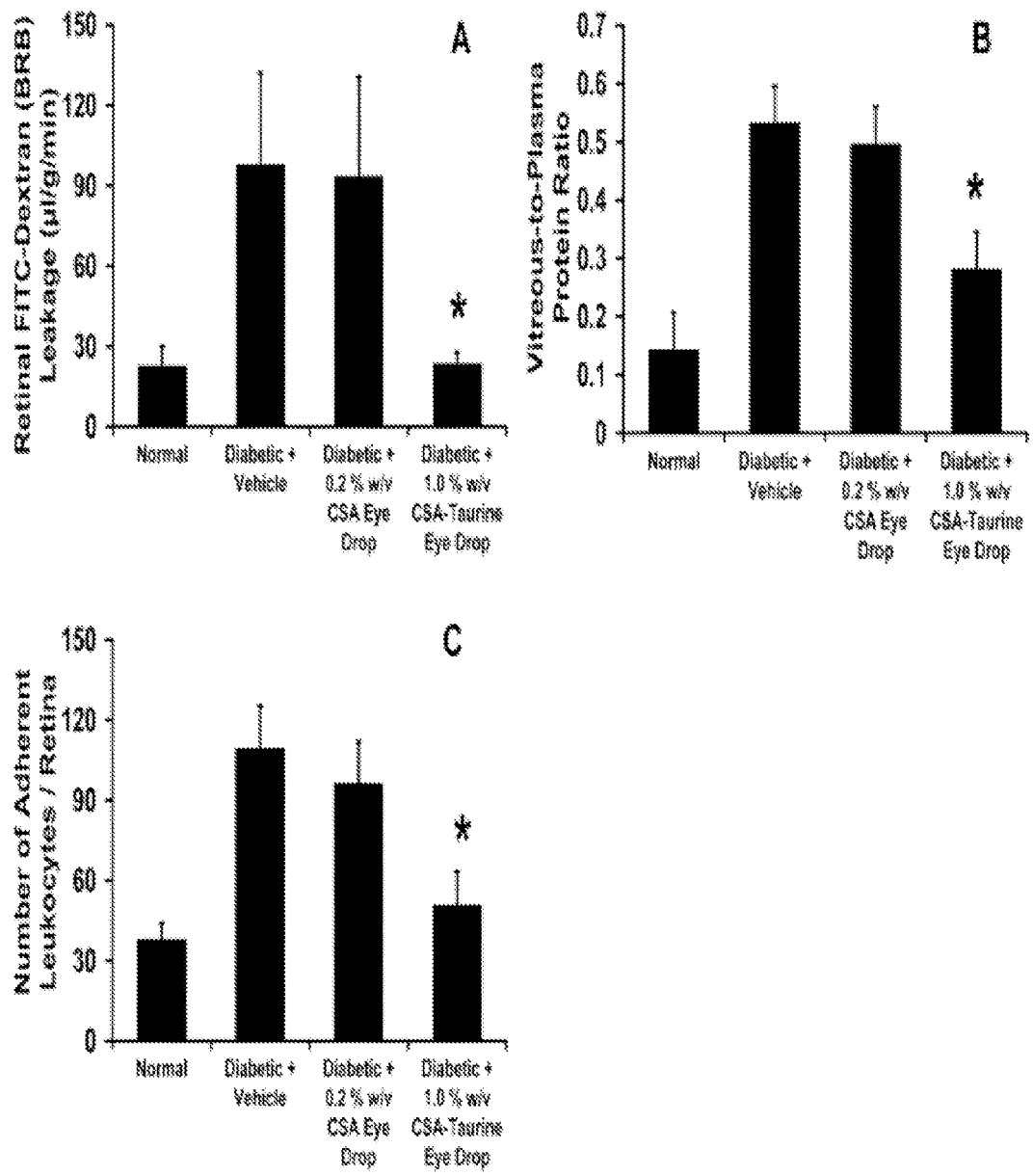
FIG. 13A-C are graph showing the ability of eye drops of 1% w/v celecoxib succinamidic acid-taurine was effective in reducing the blood retinal barrier leakage at the end of 2 months treatment in STZ-induced diabetic animals as assessed by A) FITC-Dextran (4 Kda) leakage assay, B) Vitreous to plasma protein ratio; and C) leukostasis. Data represents mean±sd (n=6-8 eyes, 3-4 animals; * Significantly different from diabetic+Vehicle group, Student's t-test, p<0.05).

Blood retinal barrier leakage was assessed via retinal FITC-dextran leakage and vitreous-to-plasma protein ratio. As represented in FIG. 13A, diabetic animals treated with vehicle (PBS, pH 7.4) had almost 4-fold higher retinal barrier leakage (mean±s.d.=97.80±34.59 μl/g/min) at the end of 2-months when compared to normal animals (mean±s.d.=22.83±7.21 μl/g/min). Animals treated with 0.2% w/v C-SA solution did not show any significant reduction in the leakage (mean±s.d.=93.66±37.08 μl/g/min). On the other hand, animals treated with the double pro-drug of celecoxib (C-SA-T, 1.0% w/v solution) showed significant reduction in the leakage (mean±s.d.=23.64±4.20 μl/g/min). C-SA-T was able to bring down the leakage levels close to that assessed in the normal animals.

Vitreous-to-Plasma Protein Ratio

As represented in FIG. 13B, normal animals demonstrated an average vitreous-to-plasma protein ratio of 0.14±0.03, whereas diabetic animals had an average value of 0.54±0.10, approximately 4-fold higher than normal animals. Animals treated with 0.2% w/v C-SA solution demonstrated an average vitreous-to-plasma protein ratio of 0.49±0.11, which was not significantly different than diabetic animals. On the other hand, animals treated with 1.0% w/v C-SA-T solution demonstrated an average vitreous-to-plasma protein ratio of 0.28±0.06 which was significantly lower than the diabetic animals treated with plain vehicle. The rank order for the vitreous-to-plasma protein ratio among various groups of animals was: diabetic≥diabetic+0.2% w/v C-SA treatment>diabetic+1.0% w/v C-SA-T treatment≥normal (Student's t-test, p-value<0.001).

Retinal Leukostasis

Adhesion of leukocytes to the retinal vasculature is another marker of the disease progression. Leukocyte count was monitored under fluorescence microscope for all groups of animals. Mean retinal leukocyte count in normal, diabetic+vehicle, diabetic+0.2% w/v C-SA, and diabetic+1.0% w/v C-SA-T groups was found to be 32±7, 114±19, 95±12, and 47±10, respectively, which clearly indicated that the double prodrug of celecoxib (C-SA-T) was effective in reducing the retinal leukocytes in diabetic retinopathy. The rank order for the retinal leukostasis among various groups of animals was: diabetic≥diabetic+0.2% w/v C-SA treatment>diabetic+1.0% w/v C-SA-T treatment≥normal (Student's t-test, p-value<0.001). See FIG. 13C.

Example 3

Plain polymeric PLGA microspheres and PLA nanospheres were prepared using an emulsion solvent evaporation method. Plain PLGA microspheres were prepared by dissolving 100 mg of polymer in 1 ml of DCM followed by dispersion of polymer solution into 10 ml of 2% aqueous poly vinyl alcohol solution under homogenization at 10,000 rpm for 1 min (Virtishear Cyclone®, USA). The prepared O/W emulsion was further transferred into 100 ml of 2% aqueous poly vinyl alcohol solution under homogenization at 15000 rpm for 5 min using a Virtishear Cyclone® Homogenizer. The organic solvent was then evaporated from the final 2% aqueous polyvinyl alcohol solution by stirring for 3 hr at room temperature. Subsequently, the microspheres were separated by centrifugation (Beckman, USA) at 12000 rpm for 15 min at 4° C. The microsphere pellet was suspended in 50 ml of distilled water and lyophilized (Lanconco Triad, USA) for 24 hr to obtain dry microspheres. Plain PLA nanospheres were prepared by dissolving 100 mg of polymer in 1 ml of DCM and 200 μl of water was dispersed into polymer solution and sonicated (Misonix Inc., USA) for 1 min at a power level of 10 W on ice to prepare the primary emulsion. This was later dispersed in 50 ml of 2% aqueous polyvinyl alcohol and sonicated for 5 min at 30 W. Subsequently, the PLA nanospheres were collected, and lyophilized by a similar procedure described above.

Example 4

Figure 14:
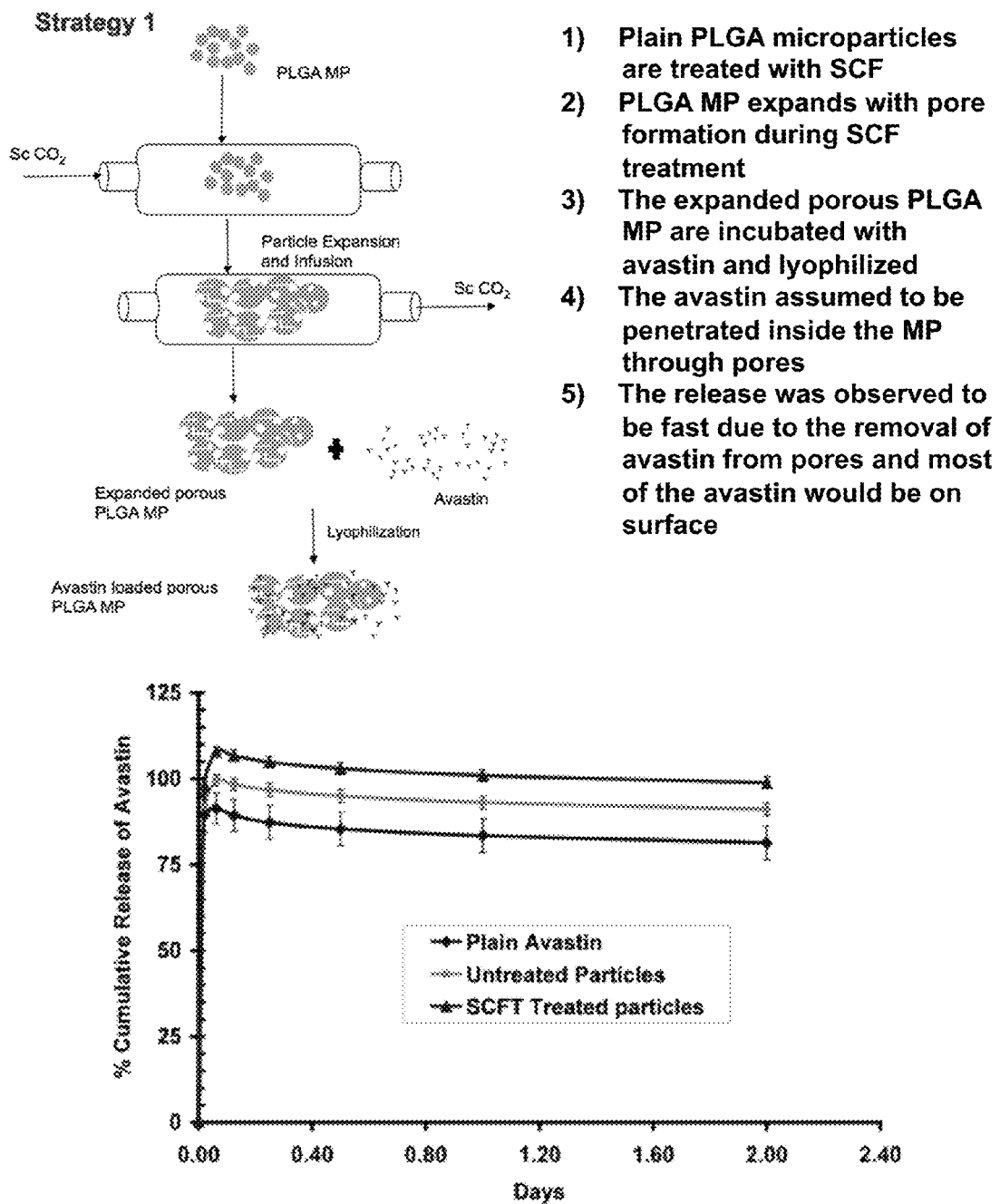
FIG. 14 is a schematic showing loading of SCF treated PLGA microparticles with bevacizumab and the cumulative release rate of bevacizumab from those microparticles.

Supercritical fluid pressure quench technology was used for expansion and porosification of blank PLGA microspheres and then bevacizumab was filled into porous microspheres. Briefly, 50 mg of plain PLGA microspheres were placed in a high pressure vessel and exposed to SC $CO_2$ at a pressure of 1150-1200 psi and a temperature of 33'C for 30 min. After completion of the SC $CO_2$ exposure, the pressure was released over a minute and the particles were collected. Subsequently, bevacizumab was filled into pores by incubating 100 µl of bevacizumab solution equivalent to 2.5 mg for 30 min and lyophilized overnight. In vitro release of bevacizumab was carried out in PBS pH 7.4 and bevacizumab content was estimated using micro BCA assay (FIG. 14).

Example 5

In an another approach, bevacizumab was encapsulated into PLGA microspheres by first coating 2.5 mg of bevacizumab in 100 µl on 50 mg of plain PLGA microspheres through lyophilization followed by their exposure to supercritical $CO_2$ as explained example 4. In vitro release of bevacizumab was carried out in PBS pH 7.4 and bevacizumab content was estimated using micro BCA assay (FIG. 15).

Example 6

A novel supercritical infusion and pressure quench technology was developed for preparing nanospheres in porous microspheres (NPinPMP) in order to sustain bevacizumab release. In this technology, plain PLA nanospheres were coated with bevacizumab by lyophilization and further mixed with plain PLGA microspheres and exposed to supercritical $CO_2$. Briefly, 100 µl of bevacizumab solution (2.5 mg) was added to 50 mg of PLA nanospheres and incubated at 4'C for 30 min and lyophilized overnight (B-PLA NP). Later, bevacizumab coated PLA nanospheres were mixed with plain PLGA microspheres and placed in a high pressure vessel. The particles were exposed to SC $CO_2$ at a pressure of 1150-1200 psi and a temperature of 33° C. for 30 min. After SC $CO_2$ exposure, the pressure was released over a minute and the particles were collected. In vitro release of bevacizumab was carried out in PBS pH 7.4 and bevacizumab content was estimated using micro BCA assay (FIG. 16). The bevacizumab activity was measured by ELISA method. The bevacizumab conformational and structural stability in the in vitro release study was evaluated by size exclusion chromatography, circular dichorosim spectroscopy, and by gel electrophoresis. The in vivo delivery of bevacizumab was monitored non-invasivley after intravitreal injection in rat model.

Activity of Bevacizumab in Release Samples

Figure 19:
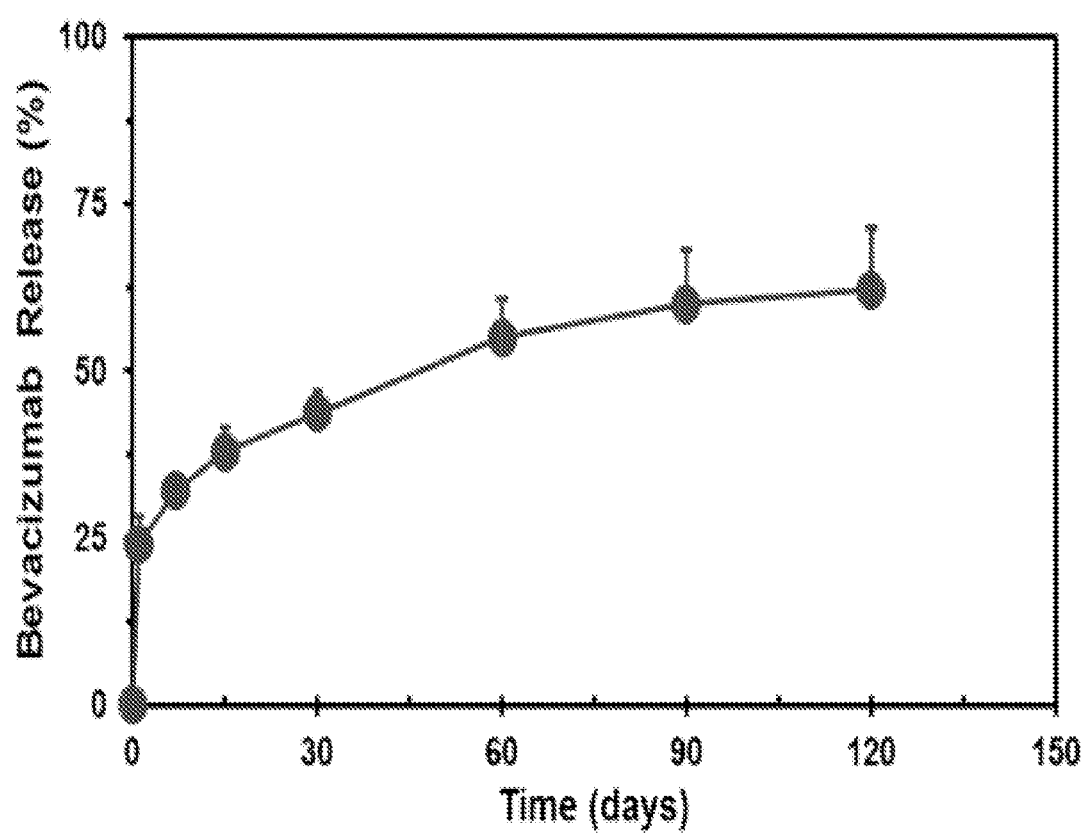
FIG. 19 is a graph showing the cumalitve in vitro release rate of bevacizumab from exemplary particle in particle (PinP) compositions.

Activity of bevacizumab released from NPinPMP was evaluated by sandwich ELISA method. The ELISA plate (BD life sciences, USA) was coated with 100 µl of 0.1 µg/ml of VEGF-165 in 50 mM sodium carbonate buffer, pH 9.6 and incubated overnight at 4° C. After overnight incubation, the plate was washed with wash buffer thrice, blotted, and air dried. Afterwards, 300 µl of blocking solution (0.5% BSA & 0.05% Tween 20 in PBS pH 7.4) was added to each well and incubated in dark for 1 hr. Then, the plate was washed with wash buffer thrice, blotted, and dried. The bevacizumab standards were prepared (0.5-50 ng/ml) in dilution buffer and incubated in dark for 2 hr. Subsequently, 100 µl of each released sample was added to the respective wells. After 2 hr incubation, plate was washed with wash buffer thrice, blotted, and dried. The secondary goat anti-human IgG (FC) antibody was diluted (1:10000) in TBS (Tris-buffered saline) pH 7.6-7.8 with 1% BSA and 100 µl of this solution was added to the plate and incubated in dark for 2 hr. After incubation, the plate was washed thrice with wash buffer and dried. To each well 100 µl of TMB substrate (3,3',5,5"-tetramethylbenzidine) was added and left for color development. After 30 min incubation, 50 µl of stop solution was added and absorbance was recorded at 450 nm. A similarly processed standard curve was used to quantify bevacizumab in the released samples. As shown in FIG. 19, released bevacizumab is active and has retained affinity for VEGF-165 confirming that the released bevacizumab retained binding ability to VEGF-165 for 4 months.

Stability Evaluation of Bevacizumab in Release Samples by Size Exclusion Chromatography (SEC)

Formation of soluble aggregate sand degradation products of bevacizumab released from NPinPMP was evaluated using size exclusion chromatography (SEC). A silica based size exclusion column (TSK® Gel G3000SWX) having 5 µm particle diameter, with dimensions of 7.8 mm×30 cm, and pore size of 250 Angstroms was used. The mobile phase was an aqueous solution of 0.182 M $KH_2PO_4$, 0.018 M $K_2HPO_4$ and 0.25 M KCl at pH 6.2. Flow rate of the mobile phase was 0.50 ml per minute. A UV detector scanning over the wavelength of 210-400 nm was used to detect the eluents from the size exclusion column.

Figure 21:
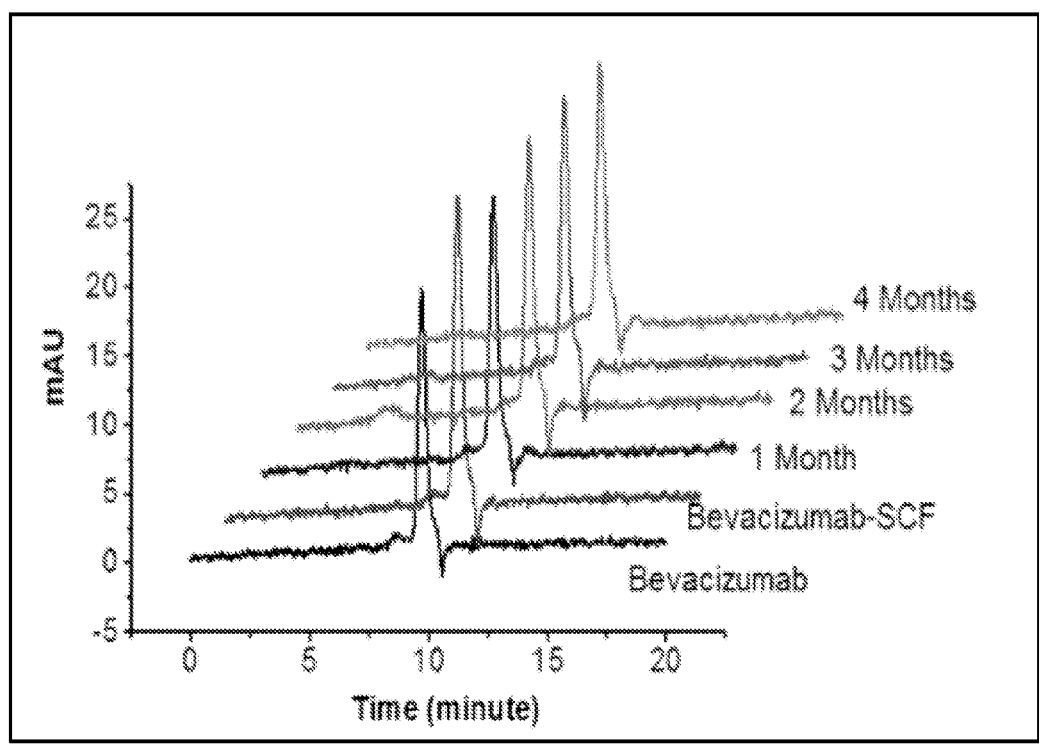
FIG. 21 is a size exclusion chromatogram of native, supercritical $CO_2$ treated bevacizumab and in vitro release of bevacizumab from exemplary PinP compositions.
Figure 22:
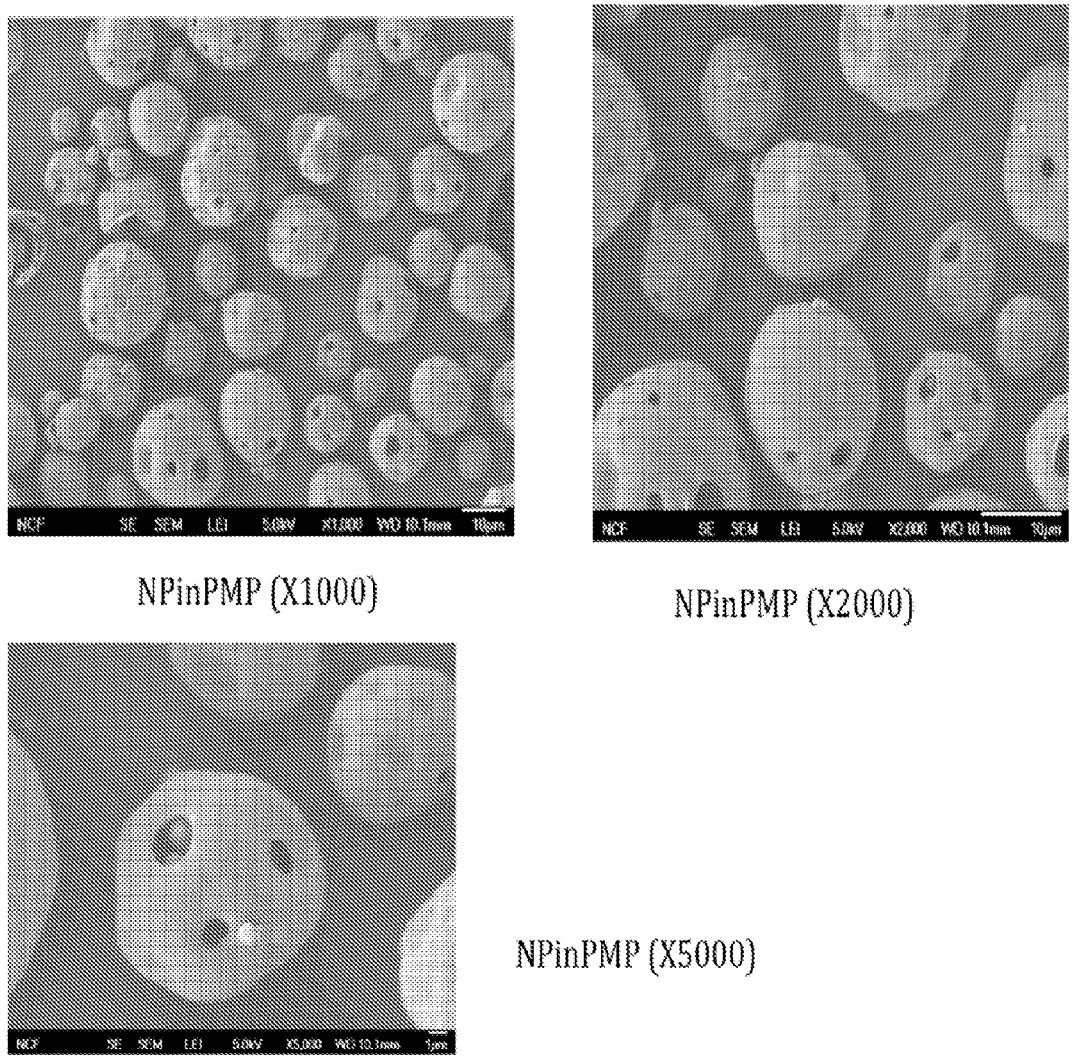
FIG. 22 are scanning electron microscopy pictures of PLA nanoparticles infused into porous PLGA microparticles (NPinPMP).

As shown in FIG. 21, analyses of SEC chromatograms of released bevacizumab showed the presence of a single prominent monomeric peak of bevacizumab at 8.1 min. The single observed peak suggests that physical and chemical stability of bevacizumab was maintained at 37° C. over a 4 month release time.

Conformational Stability Evaluation of Bevacizumab in Release Samples by Circular Dichroism (CD)

The change in the secondary structure of bevacizumab after SC $CO_2$ exposure and in the in vitro release samples was determined using circular dichorism (CD) spectroscopy (Photophysics, USA). The samples at equal protein concentrations were taken in a stain free quartz cuvette with a path length of 1 mm and spectra were recorded at 25° C. The data was collected at 1 nm step size in the 200-260 nm wavelength region.

Figure 20:
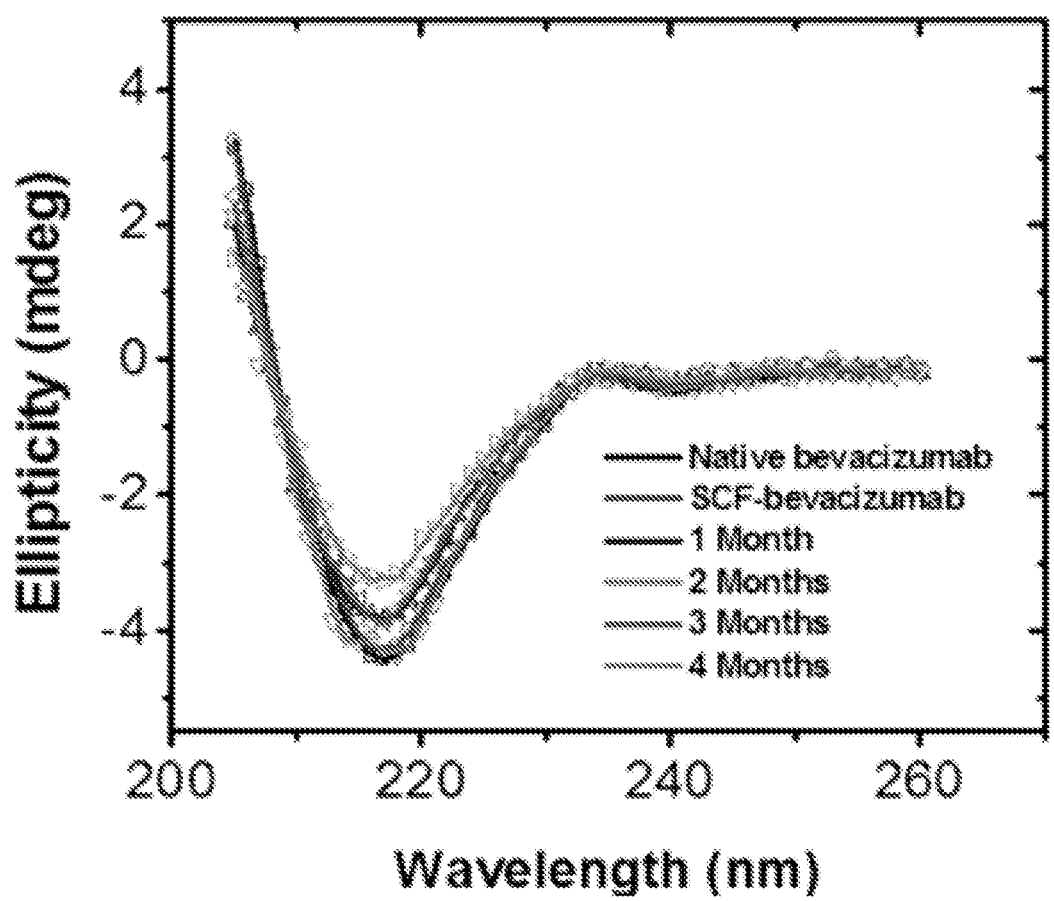
FIG. 20 is a graph showing the circular dichorism (CD) spectra of native bevacizumab, supercritical treated $CO_2$ bevacizumab, and bevacizumab from in vitro release samples (1, 2, 3, and 4 months).

As shown in FIG. 20, Circular dichroism spectrum of native bevacizumab show a peak at 218 nm, indicating the presence of a higher percentage of beta sheet like structures, which is consistent with the rich beta-sheet rich conformations of known antibodies. Released bevacizumab from exemplary PinPs at 1, 2, 3 and 4 month time points showed CD spectra similar to native bevacizumab. The observed spectra indicate that the bevacizumab's secondary structure was not significantly changed during the release study.

Evaluation of Bevacizumab Degradation in Release Samples by Gel Electrophoresis

The degradation and aggregation of bevacizumab from in vitro release samples was assessed by both reducing and non-reducing gel electrophoresis. Gel electrophoresis was performed using 4-20% SDS-PAGE precast gradient gel. Samples were prepared by taking 30 µl of each sample equivalent to 10 µg of bevacizumab and 15 µl of 2× loading dye followed by boiling for 5 min and then centrifuged at 15000 rpm for 5 min (Beckman Avanti 30, Beckman Coulter, Inc. USA). Each sample (40 µl) was loaded on precast gel and electrophoresed for 2 hr at 20 mA. Subsequently, the gel was stained with Coomassie Blue R-250, de-stained and visualized under Gel-DOC system (Bio-Rad Laboratories, USA).

Figure 23:
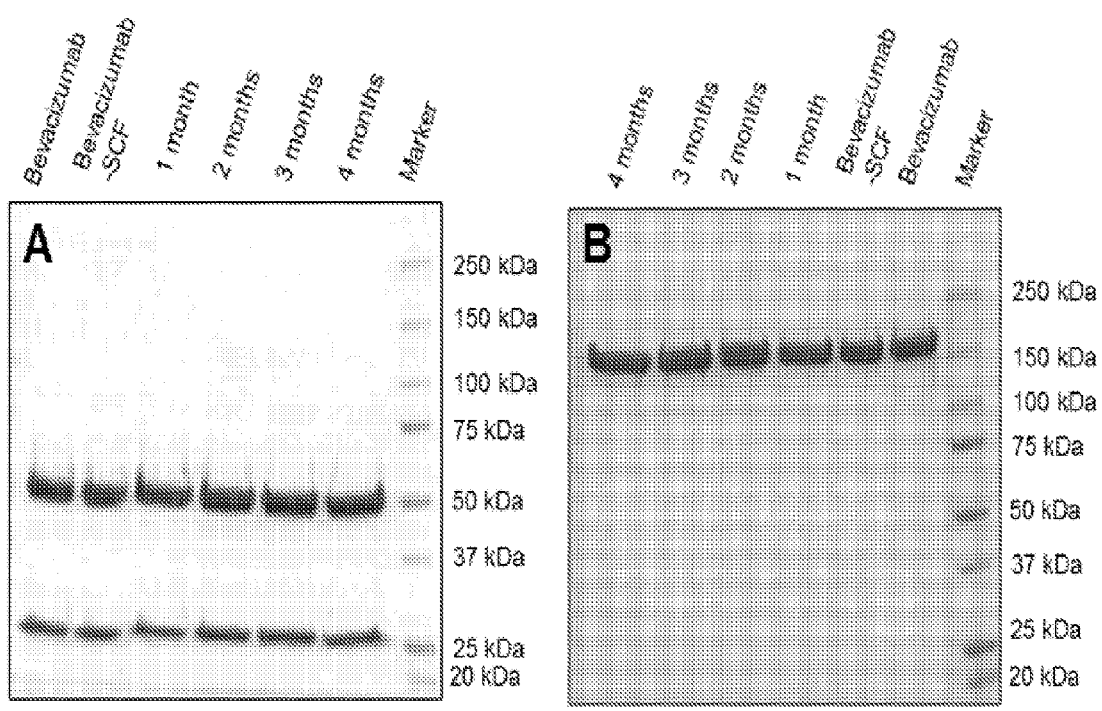
FIG. 23 is a picture of SGS PAGE gels demonstrating the results of a stability evaluation of native bevacizumab, supercritical treated $CO_2$ bevacizumab, and bevacizumab from in vitro release samples after 1, 2, 3, and 4 months. Panel A is a reducing gel. Panel B is a non-reducing gel.

As shown in FIG. 23, the SDS-PAGE data indicate the absence of degradation and/or aggregation of bevacizumab in the release samples over a 4 month period.

In Vivo Delivery of Bevacizumab in Rats

In vivo delivery of bevacizumab was evaluated following intravitreal administration of Alexa Fluor 488 conjugated bevacizumab in NPinPMP in a rat model. Rats were anesthetized by intraperitoneal injection of ketamine (35 mg/kg)/xylazine (5 mg/kg) and once the rats were under anesthesia, betadine solution was applied on the eye surface, and intravitreal injections were made using a 30-G needle. The rat eyes were injected with Alexa-bevacizumab encapsulated NPinPMP formulation (1.8 µg of Alexa-bevacizumab plus unlableled bevacizumab of 5.4 µg in/5 µl; 300 mg particles/1 ml PBS pH 7.4) and as a control Alexa-bevacizumab at equivalent concentration (7.2 µg/5 µl) was injected. Ocular fluorescence due to the release of Alexa-bevacizumab was monitored periodically using Fluorotron Master™ (Ocumetrics, CA, USA) until the fluorescence reached the lower detection limit or baseline. Baseline fluorescence values of eyes were monitored before injecting the formulations. At each time point, three fluorometric scans were taken and the mean value was used. Standard curve for Alexa-bevacizumab at different concentrations was obtained using a cuvette and ocular fluorophotometry with a rat lens adapter. The standard curve was used to convert fluorescein equivalent concentrations provided by fluorophotometer to actual Alexa-bevacizumab concentration.

After intravitreal injection of Alexa-bevacizumab encapsulating NPinPMP, and soluble alexa-bevacizumab, the concentration distribution of bevacizumab along the eye optical axis was determined indirectly by measuring the alexa fluorescence intensity distribution (equivalent of sodium fluorosciene concentration) curve along axial planes, indicated as data points in an anterior to posterior direction. The fluorescence scans revealed sustained delivery of Alexa-bevacizumab from NPinPMP compared to solution. Fluorescein equivalent concentrations reported by Fluorotron Master were converted to Alexa-bevacizumab concentrations. The Alexa-bevacizumab concentration in the vitreous region from solution and NPinPMP group at different time points was plotted. Only the concentrations of the labeled bevacizumab are reported.

Figure 24:
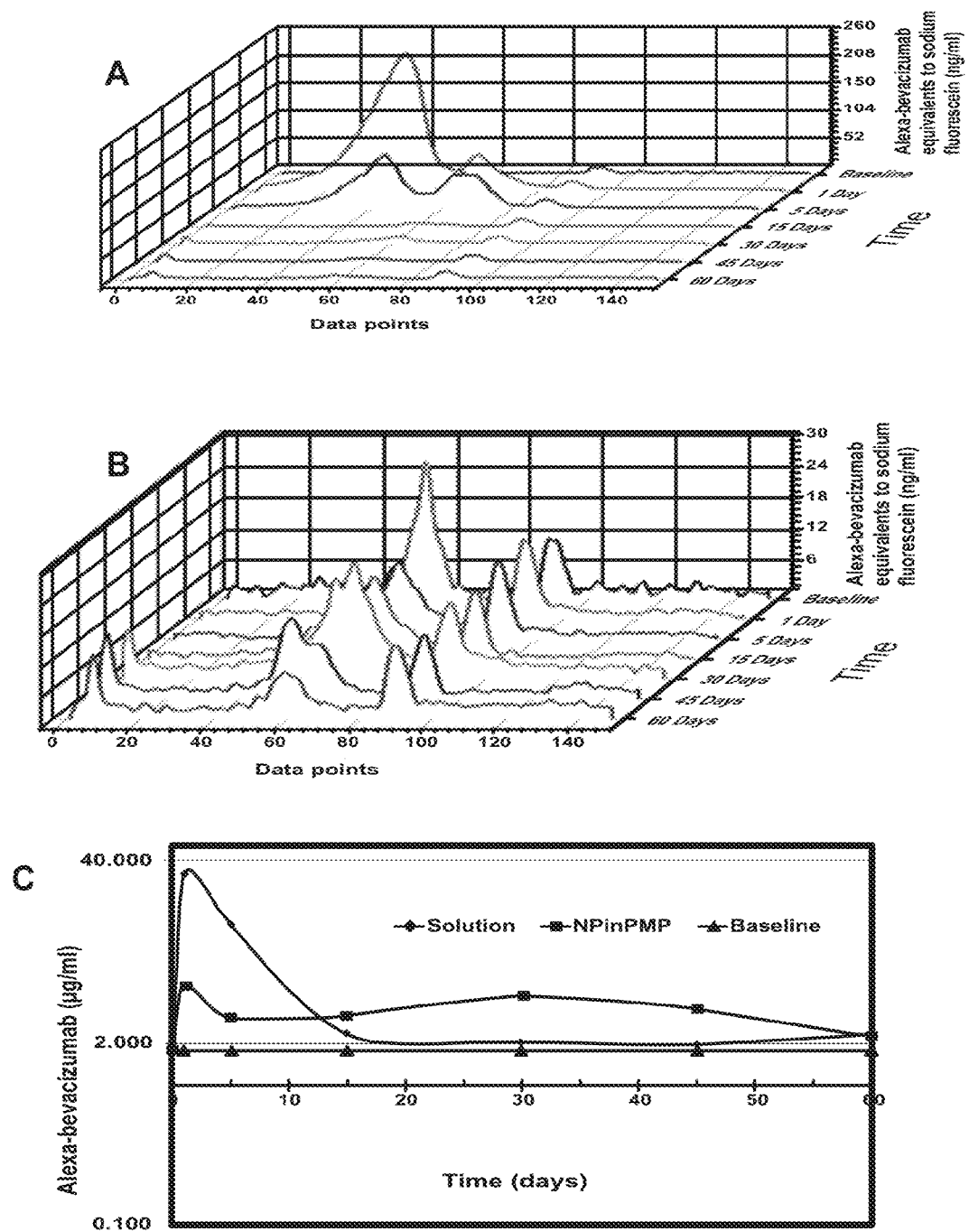
FIG. 24 are graphs depicting the results of non-invasive ocular fluorophotometry of rat eyes after intravitreal injection of A) Alexa-bevacizumab solution and B) Alexa-bevacizumab loaded in an exemplary PinP composition. Panel C show the fluorescence levels of Alexa-bevacizumab alone and Alexa-bevacizumab in PiP up to 60 days post-delivery.

Before intravitreal injection, the baseline fluorescence readings of normal eyes were taken and the baseline fluorescence concentration was found to be 1.78 µg/ml. As shown in FIG. 24, the Alexa-bevacizumab solution injected group showed Alexa-bevacizumab concentration of 32 µg/ml on day 1 and reduced to 2.2 µg/ml by day 15 indicating rapid elimination from vitreous region. In NPinPMP injected group the Alexa-bevacizumab concentration in the vitreous on day 1 was found to be 5 µg/ml and the Alexa-bevacizumab concentration was 3.5 µg/ml on day 45. However, by the end of day 60, the Alexa-bevacizumab concentration was observed to be 2.2 µg/ml, reaching baseline reading. The observed data indicate an ability to achieve sustained in vivo delivery of bevacizumab from an exemplary PinP composition.

Example 7

Confocal microscopy study was used to confirm the infusion of bevacizumab coated PLA nanospheres inside the porous PLGA microspheres by SC $CO_2$ treatment. Nile red loaded PLA nanospheres and 6-coumarin loaded PLGA microspheres were prepared using emulsion solvent evaporation method. Nile red and 6-coumarin (100 µg/100 mg polymer) were dissolved in polymer solution of PLA and PLGA, respectively before the particle preparation. 6-coumarin loaded PLGA microspheres and the mixture of Nile red loaded PLA NP and 6-coumarin loaded PLGA MP at a weight ratio of 1:9 were subjected to SC $CO_2$. The SCF conditions were about 1200 psi for 30 minutes at 33° C. The SC $CO_2$ treated particles were observed under confocal microscopy (Leica Microsystems, USA) at different magnifications (10, 20 & 100×). Further, Z-stack confocal imaging was adopted to capture the localization of Nile red in the 6-coumarin loaded PLGA microspheres. Images were captured at an interval of 0.25 µm. Nile red excitation was done at 561 nm and fluorescence images were captured using a red filter. Similarly, 6-coumarin excitation was done at 488 nm and the fluorescence image was captured using a green filter.

Figure 17:
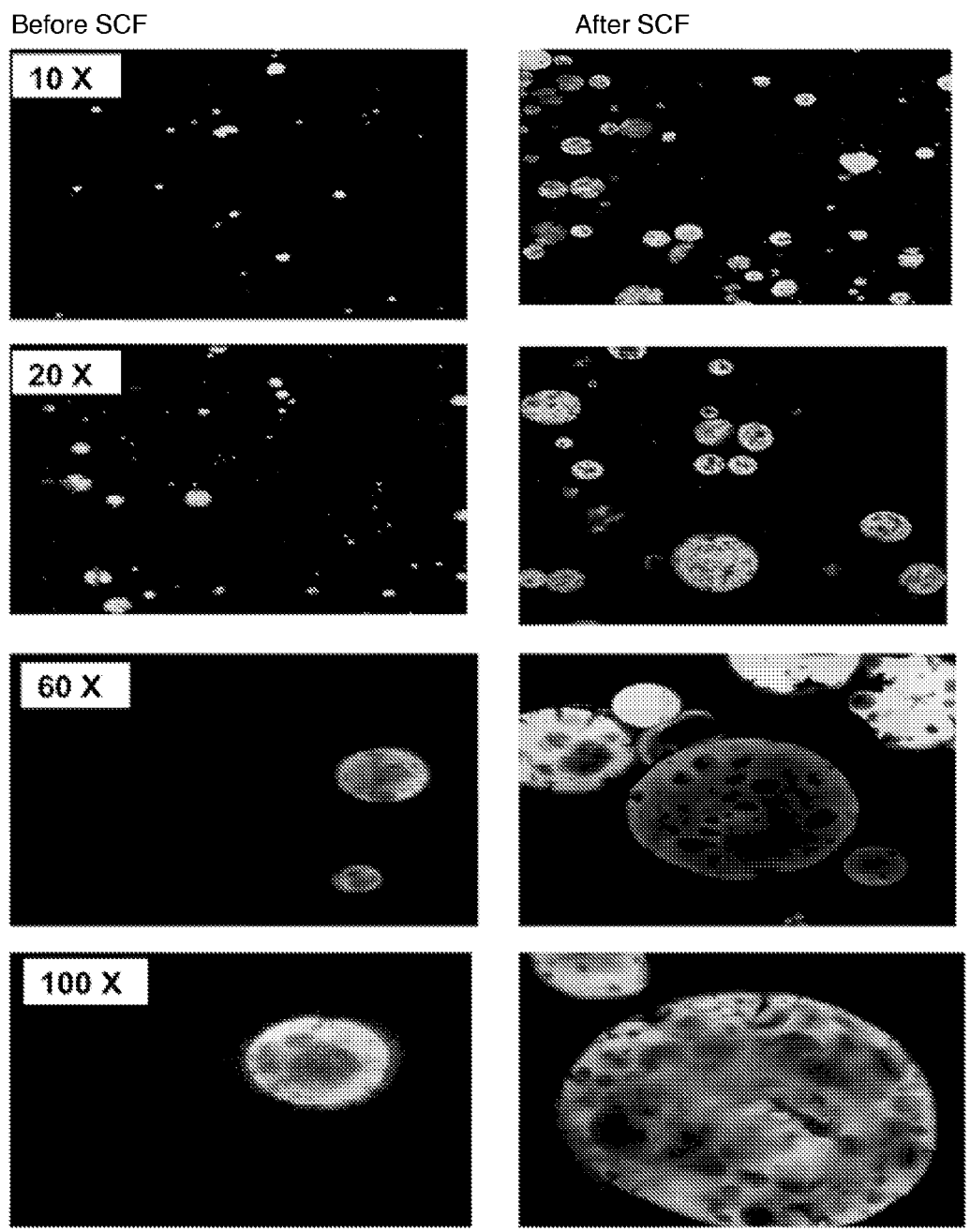
FIG. 17 are a series of confocal micrographs at increasing resolution showing the surface areas of PLGA microparticles before and after treatment with SCF.
Figure 18:
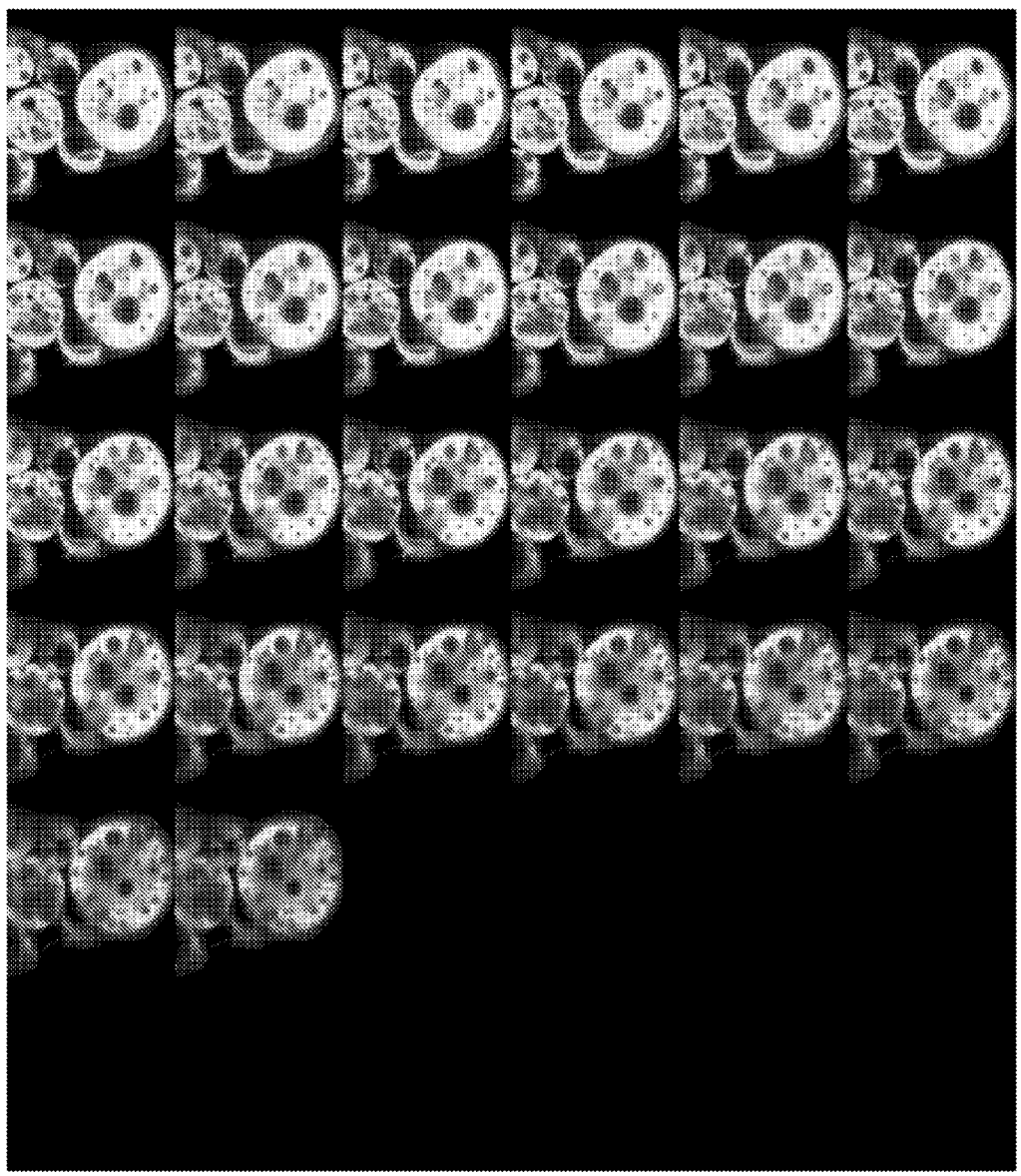
FIG. 18 is a panel of confocal micrographs showing the infusion of PLGA microparticles with PLA nanoparticles after exposure to SCF.

The confocal images of expanded porous PLGA MP and NPinPMP formulation were shown in FIGS. 17 and 18 and indicated the expansion of PLGA microsphere with pore formation after SC $CO_2$ exposure. After SC $CO_2$ treatment, the red signal of Nile red was observed to be surrounded by green signal of 6-Coumarin indicating the infusion of PLA NP inside the expanded PLGA MP. The Z sectioning image of NPinPMP formulation showed the localization of Nile red loaded NP inside the expanded 6-Coumarin loaded PLGA microspheres.

Surface morphology of gold coated PinP, were visualized using a scanning electron microscope (JSM-6510, Jeol USA, Inc., CA) at different magnifications ranging from 1000× to 5000×. As shown in FIG. 19, SCF leads to the expansion of PLGA MP with pore formation. Also, from the SEM images it was evident that PLA NPs were encapsulated inside the expanded porous PLGA MP.

Example 8

The applicability of PinP for protein sustained release was evalauted using another protein His-LEDGF$_{1-326}$. NPinPMP encapsulating His-LEDGF$_{1-326}$ were prepared as explained in Example 6. In vitro release and in vivo delivery of His-LEDGF$_{1-326}$ from NPinPMP was performed.

In Vitro Cumulative Release of His-LEDGF$_{1-326}$

Figure 25:
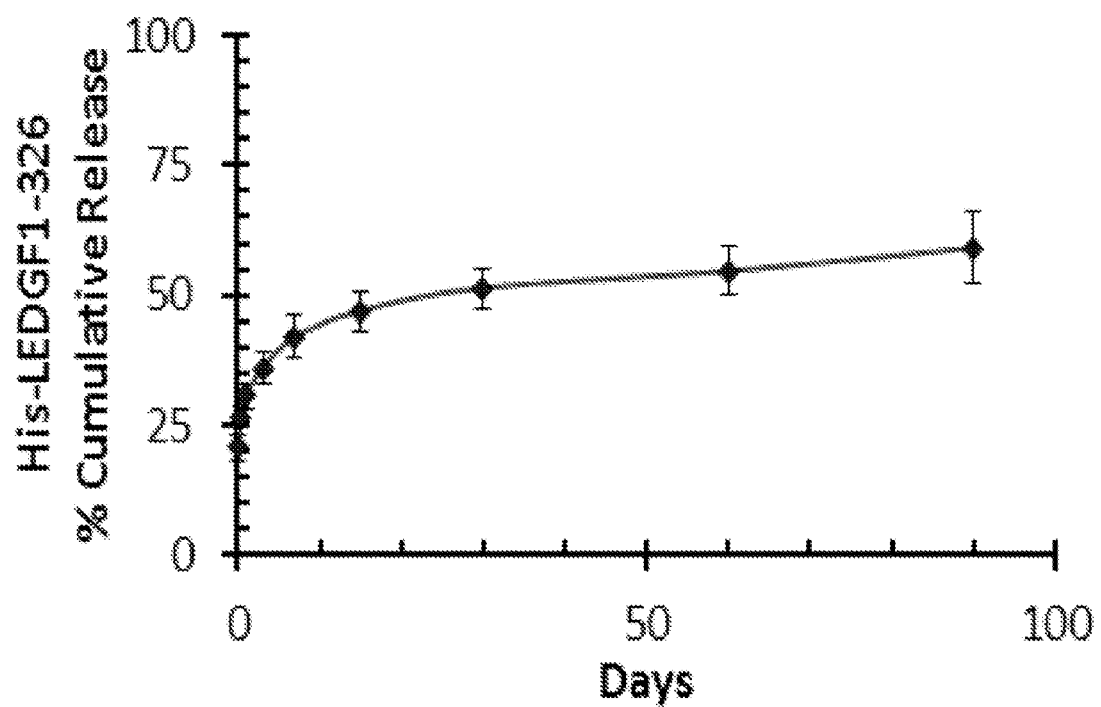
FIG. 25 is a graph showing the cumaltive release of His-LEDGF$_{1-326}$ from exemplary PinP compositions.

His-LEDGF$_{1-326}$ encapsulated NPinPMP were evaluated for in vitro release in PBS pH 7.4. Particles (2-3 mg) were weighed and dispersed in 1 ml of PBS pH 7.4 and incubated at 37° C. under shaking at 200 rpm (Max Q shaker incubator). At predetermined time points the suspended particles were centrifuged at 13,000 g for 15 min and the supernatant was collected. The pellet comprising particles was re-suspended in 1 ml of fresh PBS pH 7.4 and incubated. The His-LEDGF$_{1-326}$ content in the samples was estimated using micro BCA assay as per the manufacturer's instructions (Pierce Biotechnology, IL, USA). The in vitro cumulative data showed the sustained release of His-LEDGF$_{1-326}$ from NPinPMP. As shown in FIG. 25, a cumulative 60% release of His-LEDGF$_{1-326}$ was observed by the end of 3 months.

In Vivo Delivery of His-LEDGF$_{1-326}$ in Rats

In vivo delivery of His-LEDGF$_{1-326}$ was evaluated following intravitreal administration of Alexa Fluor 488 conjugated His-LEDGF$_{1-326}$ in NPinPMP in a rat model. No unlabeled LEDGF$_{1-326}$ was used in the NPinPMP. The rat eyes were injected with Alexa-His-LEDGF$_{1-326}$ encapsulated NPinPMP (6.0 µg of His-LEDGF$_{1-326}$/5 µl) and as a control Alexa-His-LEDGF$_{1-326}$=at equivalent concentration (1.5 μg labeled protein and 4.5 μg unlabeled protein/5 μl) was injected. This ratio allowed us to start with a similar fluorescence intensity for both groups to begin with. Ocular fluorescence due to the release of Alexa-His-LEDGF$_{1-326}$ was monitored periodically using Fluorotron Master™ (Ocumetrics, CA, USA) until the fluorescence reached the lower detection limit or baseline. Baseline fluorescence values of eyes were monitored before injecting the formulations. At each time point, three fluorometric scans were taken and mean value was used. Standard curve for Alexa-His-LEDGF$_{1-326}$ at different concentrations was obtained using a cuvette and ocular fluorophotometry with a rat lens adapter. The standard curve was used to convert fluorescein equivalent concentrations provided by fluorophotometer to actual Alexa-His-LEDGF$_{1-326}$ concentration.

Figure 26:
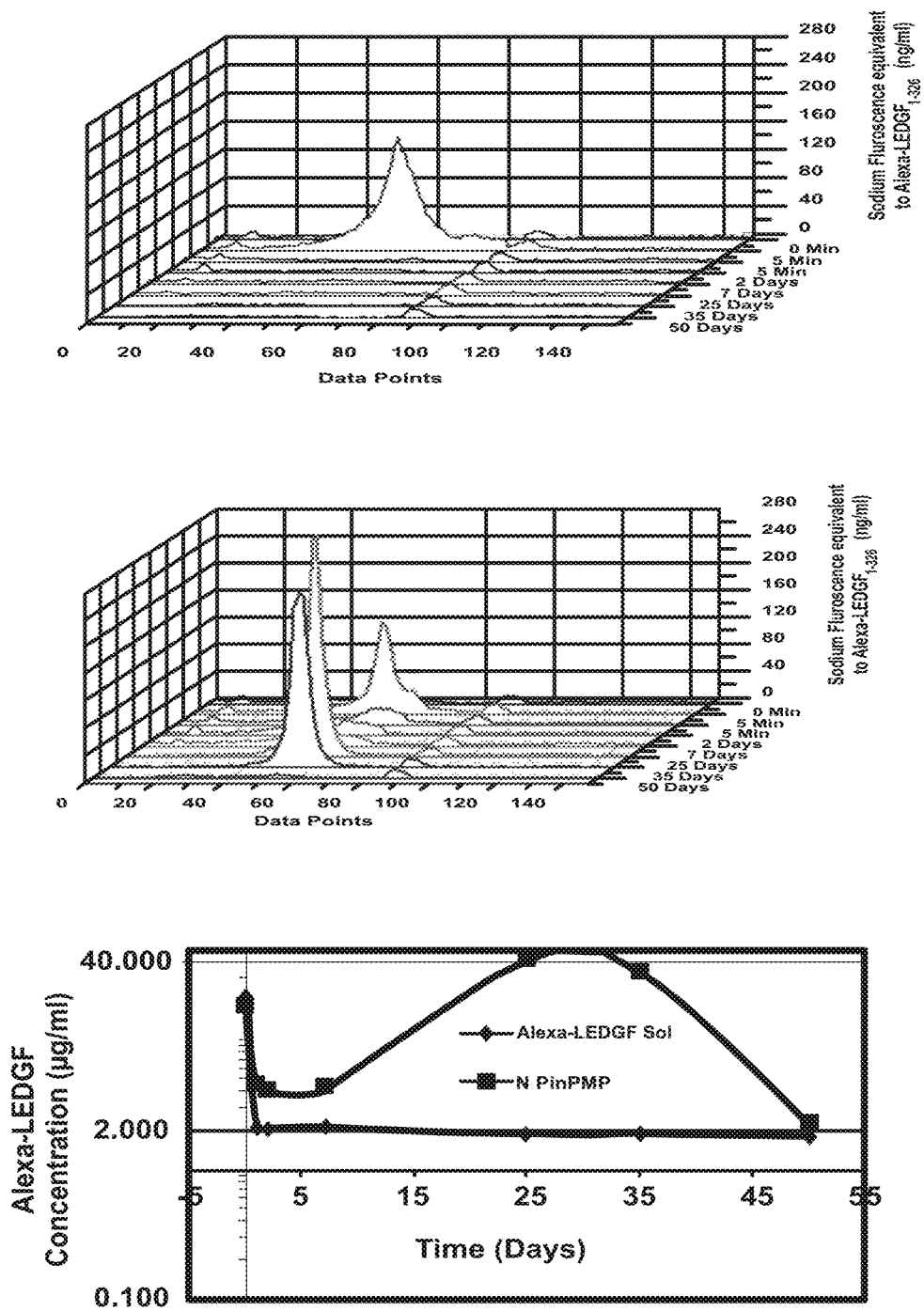
FIG. 26A-C are graphs showing the results of non-invasive ocular fluorophotometry after intravitreal injection in rat eyes of A) Alexa-His-LEDGF$_{1-326}$ solution and B) Alexa-His-LEDGF$_{1-326}$ loaded in PinP. Panel C shows the His-LEDGF$_{1-326}$ concentrations for the PinP and solution injected groups.

After intravitreal injection of Alexa-His-LEDGF$_{1-326}$ encapsulating NPinPMP, and soluble Alexa-His-LEDGF$_{1-326}$, the concentrations distribution of His-LEDGF$_{1-326}$ along the eye optical axis was determined indirectly by measuring the alexa fluorescence intensity distribution (equivalent of sodium fluorescene concentration) curve along axial planes, indicated as data points in an anterior to posterior direction. The fluorescence scans revealed sustained delivery of Alexa-His-LEDGF$_{1-326}$ from NPinPMP compared to solution. Fluorescein equivalent concentrations reported by Fluorotron Master were converted to Alexa-His-LEDGF$_{1-326}$ concentrations. The Alexa-His-LEDGF$_{1-326}$ concentration in the vitreous region from solution and NPinPMP group at different time points was plotted. Only the concentrations of the labeled bevacizumab are reported. Before intravitreal injection, the baseline fluorescence readings of normal eyes were taken and the baseline fluorescence concentration was found to be 2.03 μg/ml. As showing in FIG. 26, the Alexa-His-LEDGF$_{1-326}$ solution injected group showed Alexa-His-LEDGF$_{1-326}$ concentration of 2.02 μg/ml on day 1 indicating rapid elimination from vitreous region. In NPinPMP injected group the Alexa-His-LEDGF$_{1-326}$ the initial concentration in the vitreous was found to be 18.23 μg/ml and the Alexa-His-LEDGF$_{1-326}$ concentration above the baseline was maintained until 35th day and reached normal base line levels by end of 50 days. The observed data indicate the ability to achieve sustained in vivo release of Alexa-His-LEDGF$_{1-326}$ from an exemplary PinP composition.

REFERENCES

1. Rohdewald, P. and V. Keuth, *Evaluation of algesimetric parameters on the basis of tooth pulp stimulation in humans*. Anesth Prog, 1990. 37(1): p. 4-10.
2. Kompella, U. B., N. Bandi, and S. P. Ayalasomayajula, *Subconjunctival nano-and microparticles sustain retinal delivery of budesonide, a corticosteroid capable of inhibiting VEGF expression*. Invest Ophthalmol V is Sci, 2003. 44(3): p. 1192-201.
3. Ayalasomayajula, S. P. and U. B. Kompella, *Celecoxib, a selective cyclooxygenase-2 inhibitor, inhibits retinal vascular endothelial growth factor expression and vascular leakage in a streptozotocin-induced diabetic rat model*. Eur J Pharmacol, 2003. 458(3): p. 283-9.
4. Ayalasomayajula, S. P., A. C. Amrite, and U. B. Kompella, *Inhibition of cyclooxygenase-2, but not cyclooxygenase-1, reduces prostaglandin E2 secretion from diabetic rat retinas*. Eur J Pharmacol, 2004. 498(1-3): p. 275-8.
5. Sennlaub, F., et al., *Cyclooxygenase-2 in human and experimental ischemic proliferative retinopathy*. Circulation, 2003. 108(2): p. 198-204.
6. Cheng, T., et al., *Prostaglandin E2 induces vascular endothelial growth factor and basic fibroblast growth factor mRNA expression in cultured rat Muller cells*. Invest Ophthalmol V is Sci, 1998. 39(3): p. 581-91.
7. Saishin, Y., et al., *Inhibition of protein kinase C decreases prostaglandin-induced breakdown of the blood-retinal barrier*. J Cell Physiol, 2003. 195(2): p. 210-9.
8. Penn, J. S., et al., *Vascular endothelial growth factor in eye disease*. Prog Retin Eye Res, 2008. 27(4): p. 331-71.
9. Derevjanik, N. L., et al., *Quantitative assessment of the integrity of the blood-retinal barrier in mice*. Invest Ophthalmol V is Sci, 2002. 43(7): p. 2462-7.
10. Pow, D. V., et al., *Localization of taurine transporters, taurine, and (3)H taurine accumulation in the rat retina, pituitary, and brain*. Glia, 2002. 37(2): p. 153-68.
11. Ehinger, B., *Glial uptake of taurine in the rabbit retina*. Brain Res, 1973. 60(2): p. 512-6.
12. Ball, A. K. and D. H. Dickson, *Displaced amacrine and ganglion cells in the newt retina*. Exp Eye Res, 1983. 36(2): p. 199-213.
13. Pourcho, R. G., *Distribution of [35S] taurine in mouse retina after intravitreal and intravascular injection*. Exp Eye Res, 1977. 25(2): p. 119-27.
14. Obrosova, I. G., et al., *Antioxidants attenuate early up regulation of retinal vascular endothelial growth factor in streptozotocin-diabetic rats*. Diabetologia, 2001. 44(9): p. 1102-10.
15. Cheruvu, N. P. and U. B. Kompella, *Bovine and porcine transscleral solute transport: influence of lipophilicity and the Choroid-Bruch's layer*. Invest Ophthalmol V is Sci, 2006. 47(10): p. 4513-22.
16. Thakur, A., R. S. Kadam, and U. B. Kompella, *Trabecular meshwork and lens partitioning of corticosteroids: Implications for elevated intraocular pressure and cataracts*. Arch Ophthalmol. In press.
17. Kadam, R. S., et al., *Sclera-choroid-RPE transport of eight beta-blockers in human, bovine, porcine, rabbit, and rat models*. Invest Ophthalmol V is Sci, 2011. PMID: 21282583.

What is claimed is:
1. A compound comprising, celecoxib having the formula:

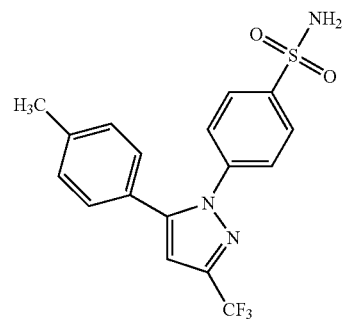 [SMILES: Cc1ccc(-c2cc(C(F)(F)F)nn2-c2ccc(S(N)(=O)=O)cc2)cc1]

wherein the terminal functional group —SO$_2$NH$_2$ is masked by binding to a multi-functional counter acid linking group, the linking group further having a taurine bound thereto.

2. The compound of claim 1 wherein the multi-functional counter acid group is selected from the group consisting of a maleate, a fumarate, a tartrate, a citrate and a succinate.

3. The compound of claim 2, wherein the multi-functional counter acid group is a succinate.

4. A composition comprising the compound of claim 1 and a pharmaceutical carrier, diluent, excipient, or a combination thereof.

5. A method of treating an ocular disease comprising administering to a patient in need thereof the composition of claim 4, wherein administration results in delivery of the composition to posterior or anterior segment tissues of the eye including retina, choroid, vitreous humor, iris, ciliary body, aqueous humor or other eye tissues.

6. The method of claim 5, wherein the composition is administered topically to the eye.

7. The method of claim 5, wherein the ocular disease is an ocular degenerative disease, an ocular vascular disease, an ocular inflammatory disease, an ocular infectious disease, glaucoma, or optic neuritis.

8. The method of claim 7, wherein the disease is diabetic retinopathy.

* * * * *